US012648818B2

(12) United States Patent
Zenisek

(10) Patent No.: US 12,648,818 B2
(45) Date of Patent: Jun. 9, 2026

(54) ACCURACY SYSTEM

(71) Applicant: Medtronic, Inc., Minneapolis, MN (US)

(72) Inventor: Todd D. Zenisek, Georgetown, TX (US)

(73) Assignee: Medtronic, Inc., Minneapolis, MN (US)

( * ) Notice: Subject to any disclaimer, the term of this patent is extended or adjusted under 35 U.S.C. 154(b) by 886 days.

(21) Appl. No.: 17/808,195

(22) Filed: Jun. 22, 2022

(65) Prior Publication Data

US 2022/0409294 A1 Dec. 29, 2022

Related U.S. Application Data

(60) Provisional application No. 63/214,107, filed on Jun. 23, 2021.

(51) Int. Cl.
*A61B 34/30* (2016.01)
*A61B 34/20* (2016.01)
*A61B 90/11* (2016.01)
*A61B 90/00* (2016.01)

(52) U.S. Cl.
CPC .............. *A61B 34/20* (2016.02); *A61B 90/11* (2016.02); *A61B 2034/2057* (2016.02); *A61B 2034/2065* (2016.02); *A61B 2034/207* (2016.02); *A61B 2090/061* (2016.02); *A61B 2090/0807* (2016.02); *A61B 2090/371* (2016.02)

(58) Field of Classification Search
CPC ......... A61B 34/20; A61B 34/30; A61B 90/11; A61B 2090/061
See application file for complete search history.

(56) References Cited

U.S. PATENT DOCUMENTS

| 5,246,448 | A | 9/1993 | Chang |
| 6,258,103 | B1 | 7/2001 | Saracione |
| 8,249,693 | B2 | 8/2012 | Kieper et al. |
| 2005/0055035 | A1 | 3/2005 | Cosman, Jr. et al. |
| 2017/0265943 | A1* | 9/2017 | Sela ........................ A61B 34/20 |
| 2020/0030038 | A1 | 1/2020 | Wang et al. |
| 2020/0405403 | A1* | 12/2020 | Shelton, IV ....... A61B 17/3421 |

FOREIGN PATENT DOCUMENTS

WO     2015052669 A1     4/2015

OTHER PUBLICATIONS

Elekta et al., "Leksell Stereotactic System", product brochure, Mar. 2020, 22 pp.

* cited by examiner

*Primary Examiner* — Vi X Nguyen
(74) *Attorney, Agent, or Firm* — Shumaker & Sieffert, P.A.

(57) ABSTRACT

An accuracy system configured to determine the accuracy of a stereotactic system The accuracy system is configured to determine a displacement between a pointer tip positioned by the stereotactic system and a target point defined by a phantom base. The accuracy system is configured to mechanically engage the phantom base when the phantom base mechanically engages the stereotactic system to determine the displacement. In examples, a gauge support mechanically engages a pin of the phantom base and determines the displacement using one or more visible indicia. In examples, a gauge frame supports one or more cameras and determines the displacement using a first image and a second image obtained by the one or more cameras. The accuracy system provides an output viewable by a practitioner to indicate the determined displacement.

20 Claims, 8 Drawing Sheets

802

Defining a displacement between a target point of a phantom base and a pointer tip

804

Providing an output viewable by a practitioner indicative of the displacement

ACCURACY SYSTEM

This application claims the benefit of U.S. Provisional Application Ser. No. 63/214,107 (filed Jun. 23, 2021), which is entitled "ACCURACY SYSTEM" and is incorporated by reference herein in its entirety.

TECHNICAL FIELD

This disclosure is related to accuracy systems for a stereotactic system.

BACKGROUND

Various types of medical delivery systems are utilized for implantation of medical devices. Such implantable devices may be adapted to allow monitoring and/or treatment of conditions or functions relating to heart, muscle, nerve, brain, stomach, endocrine organs or other organs and their related functions. The medical devices may include electrodes and/or other elements for physiological sensing and/or therapy delivery. The medical delivery systems allow the medical devices to be positioned at one or more target locations within the patient for those functions.

Stereotactic systems may be utilized to provide positional reference relative to the patient during implantation of the medical device. For example, a stereotactic system may be utilized to position a medical device (e.g., an implantable lead) in the brain of a patient to treat a variety of medical conditions, including the relief of chronic pain (e.g., via electrical stimulation of the brain) and/or the treatment of movement disorders, epilepsy, psychiatric disorders, headaches, eating, hearing, vision disorders, and others. To accurately place the medical device and avoid unintended interaction with eloquent areas of the brain, clinicians may use stereotactic systems (or a similar pointing/guiding accuracy systems) to determine coordinates within the brain describing a target site. The stereotactic apparatus may assist in guiding surgical or other instruments (e.g., catheters and electrical leads) to the target site.

SUMMARY

In general, this disclosure describes an accuracy system configured to determine the accuracy of a stereotactic system. The stereotactic system may be configured to provide positional reference relative to a patient. The accuracy system may determine a displacement between a pointer tip positioned by the stereotactic system and a target point defined by a phantom base secured to the stereotactic system. The accuracy system is configured to measure the displacement when the stereotactic system attempts (e.g., using control software or other position indexes) to position the pointer tip at the real-space target point defined by the target point of the phantom base. The accuracy system is configured to provide an output indicative of the displacement to a practitioner.

In an example, a system configured to determine an accuracy of a stereotactic frame is configured to: define an x displacement from a target point of a phantom base mechanically engaging the stereotactic frame to a pointer tip of the stereotactic frame when the pointer tip is placed at a pointer tip location, wherein the x displacement is a distance parallel to an x axis in an x-y-z coordinate system; define a y displacement from the target point to the pointer tip when the pointer tip is placed in the pointer tip location, wherein the y displacement is a distance parallel to a y axis in the x-y-z coordinate system; define a z displacement from the target point to the pointer tip when the pointer tip is placed in the pointer tip location, wherein the z displacement is a distance parallel to a z axis in the x-y-z coordinate system; and provide an output viewable by a practitioner, wherein the output indicates one or more of the x displacement, the y displacement, or the z displacement.

In an example, a system configured to determine an accuracy of a stereotactic frame is configured to: define an x-y-z coordinate system; define an x displacement from a target point of a phantom base mechanically engaging the stereotactic frame to a pointer tip of the stereotactic frame when the pointer tip is placed at a pointer tip location, wherein the x displacement is a distance parallel to an x axis in the x-y-z coordinate system; define a y displacement from the target point to the pointer tip when the pointer tip is placed in the pointer tip location, wherein the y displacement is a distance parallel to a y axis in the x-y-z coordinate system; define a z displacement from the target point to the pointer tip when the pointer tip is placed in the pointer tip location, wherein the z displacement is a distance parallel to a z axis in the x-y-z coordinate system, wherein the system is configured to at least one: define at least one of the x displacement or a the y displacement on a horizontal anatomical plane defined by the intercranial space, and define the z displacement on at least one of a medial anatomical plane defined by the intercranial space or a coronal anatomical plane defined by the intercranial space of the patient; or define one of the x displacement or the y displacement substantially parallel to an anterior or posterior direction of the patient and define the other of the x displacement or the y displacement substantially parallel to a left lateral or a right lateral direction of the patient. and define the z displacement substantially parallel to a superior or inferior direction of the patient; map the x-y-z coordinate system to a coordinate system defined by the phantom base; and provide an output viewable by a practitioner, wherein the output indicates one or more of the x displacement, the y displacement, or the z displacement mapped to the coordinate system defined by the phantom base.

In an example, a technique comprises: defining, with a system, an x displacement from a target point of a phantom base mechanically engaging the a stereotactic frame to a pointer tip of the stereotactic frame when the pointer tip is placed at a pointer tip location in proximity to the target point, wherein the x displacement is a distance parallel to an x axis in an x-y-z coordinate system; defining, with the system, a y displacement from the target point to the pointer tip when the pointer tip is placed in the pointer tip location, wherein the y displacement is a distance parallel to a y axis in the x-y-z coordinate system; defining, with the system, a z displacement from the target point to the pointer tip when the pointer tip is placed in the pointer tip location, wherein the z displacement is a distance parallel to a z axis in the x-y-z coordinate system; and providing, with the system, an output viewable by a practitioner, wherein the output indicates one or more of the x displacement, the y displacement, or the z displacement.

The details of one or more examples are set forth in the accompanying drawings and the description below. Other features, objects, and advantages will be apparent from the description and drawings, and from the claims.

DETAILED DESCRIPTION

Figure 1:
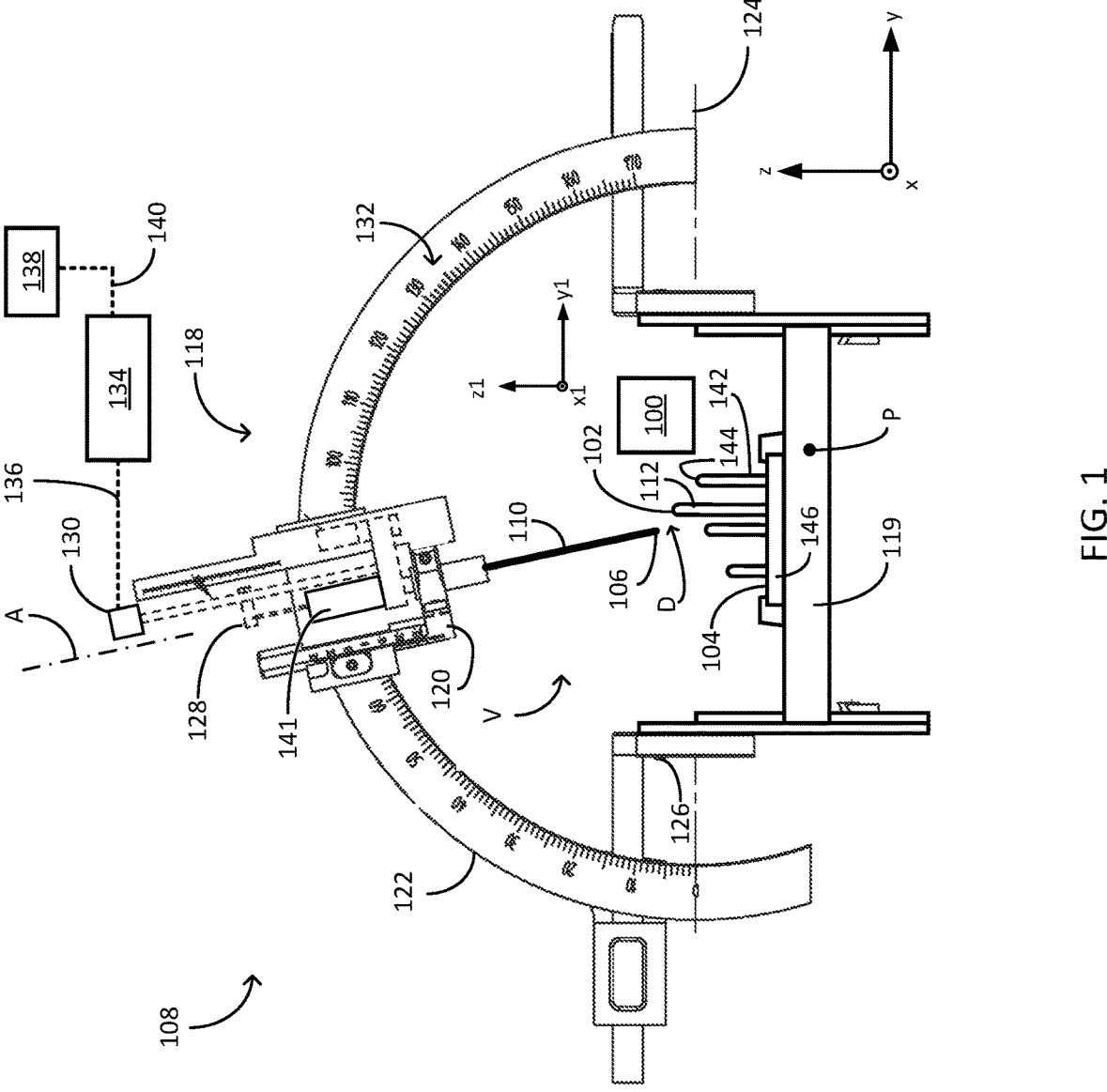
FIG. 1 is a conceptual diagram illustrating an example stereotactic system and a phantom base.

This disclosure describes an accuracy system configured to determine the accuracy of a stereotactic system configured to provide positional reference relative to a patient. The accuracy system is configured to determine a displacement between a pointer tip positioned by the stereotactic system and a target point defined by a phantom base. The displacement determined by the accuracy system provides a measure of the accuracy of the stereotactic system when the stereotactic system is utilized (e.g., using control software or other position indexes) to position the pointer tip at the real-space target point defined by the target point of the phantom base. The accuracy system is configured to determine the displacement based on a spatial comparison of the real-space target point defined by the phantom base and the actual pointer tip location achieved when an output of the stereotactic system indicates the pointer tip is located at the real-space target point. The spatial comparison serves to indicate the magnitude and the associated directions of the stereotactic system error, such that a user of the stereotactic system may be informed of the placement accuracy of the stereotactic system when the stereotactic system attempts to achieve a specific coordinate. In examples, the accuracy system spatially compares the pointer tip location of a stereotactic system intended to enable intercranial access with a target point defined by a phantom base configured to provide target points for an intercranial space.

The accuracy system may be configured to define the spatial relationship between the pointer tip location of the stereotactic system and the target point of the phantom base and provide an output indicative of the spatial relationship. The output is viewable by a practitioner. In examples, the accuracy system includes visible indicia indicating a displacement between the pointer tip location and the target point when the accuracy system defines the spatial relationship, such that a practitioner may observe the visible indicia as an indication of the displacement. In examples, the accuracy system defines the spatial relationship and determines one or more magnitudes and/or one or more directions describing the displacement, and the magnitudes and/or directions to a display viewable by a practitioner.

In examples, the accuracy system is configured to define a displacement between the pointer tip location of the stereotactic system and the target point of the phantom base in an x-direction, a y-direction, and/or a z-direction. The x-direction, the y-direction, and/or the z-direction may be directions parallel to an x axis, a y axis, and/or a z axis respectively in an x-y-z coordinate system. In examples, the stereotactic system defines the x-y-z coordinate system. In certain examples, the accuracy system is configured to define the displacement using an x1 axis, a y1 axis, and/or a z1 axis in an x1-y1-z1 coordinate system defined by the accuracy system, and the accuracy system is configured to substantially map the displacement to an x-y-z coordinate system defined by the stereotactic system, such that a practitioner may be informed of the placement accuracy of the stereotactic system using the x-y-z coordinate system employed by the stereotactic system.

The accuracy system may be configured to mechanically engage some portion of the phantom base to define the displacement. The phantom base may be configured to mechanically engage the stereotactic system, such that the phantom base provides real-space target points in a simulated intercranial space for the stereotactic system. The phantom base may include, for example, a support plate and a plurality of elongated pins extending from the support plate. A distal end of a pin may define a target point when the phantom base mechanically engages the stereotactic system. The mechanical engagement of the phantom base and the stereotactic system may cause the defined target point of the phantom base to position at a specific x-y-z coordinate describing a real-space location within the simulated intercranial space. The stereotactic system may be configured to place a pointer tip of a pointer in the vicinity of the specific x-y-z coordinate defined by the target point. For example, the stereotactic control system may include positioning software configured cause translation of the pointer tip based on an input describing the specific x-y-z coordinate. Inaccuracies of the stereotactic system may result in a displacement between the pointer tip and the target point when the stereotactic system positions the pointer tip based on the inputted x-y-z coordinate. The accuracy system disclosed herein may mechanically engage the phantom base when the phantom base is mechanically engaged with the stereotactic system, such that the accuracy system may define the displacement between the target point and the pointer tip to indicate an accuracy of the stereotactic system.

The accuracy system may be configured such that at least some portion of the accuracy system is substantially stationary relative to the phantom base when the accuracy system mechanically engages the phantom base. In examples, the accuracy system is configured such that portion of the accuracy system is substantially stationary relative to the phantom base and a positioned pointer tip when the accuracy system mechanically engages the phantom base and the phantom base mechanically engages the stereotactic system. The stability of the accuracy system relative to the phantom base and/or stereotactic system may allow the accuracy system to define the spatial relationship between the target point and the pointer tip in order to define the displacement between the target point and the pointer tip. In some examples, the accuracy system is configured to mechanically engage a pin of the phantom base. In some examples, the accuracy system may be configured to mechanically engage some portion of a support plate of the phantom base.

In examples, the accuracy system is configured to define the displacement (e.g., the x displacement, the y displacement, and/or the z displacement) between a target point and a pointer tip relative to the position of the target point. The accuracy system may be configured to define the displacement relative to any of a plurality of target points defined by the phantom base, such that the accuracy system may be selectively applied for each of the target points defined. For example, the accuracy system may be configured to define the displacement relative to a first target point defined by a first pin of the phantom base in order to define a displacement between a pointer tip and the first target point. The accuracy system may be configured to subsequently define the displacement relative to a second target point defined by a second pin of the phantom base in order to define a displacement between the pointer tip and the second target point. Hence, the accuracy system may be configured to define the displacement between a pointer tip and each target point defined by a phantom base configured to define a plurality of target points.

The accuracy system may be configured to mechanically engage a phantom base defining one or more elongated pins each defining a target point in a simulated intercranial space. A pin may extend from first end secured to a support plate of the phantom base to a second end defining the target point. The pin may include a pin body extending from the first end to the second end and defining a pin axis from the first end to the second end. In examples, the phantom base is configured to mechanically engage a stereotactic system such that each pin defines a target point that remains substantially stationary relative to the stereotactic system. Thus, the phantom base may position the target points in real-space at specific positions within the x-y-z coordinate system of the stereotactic system when the phantom base mechanically engages the stereotactic system. The accuracy system may be configured to mechanically engage the phantom base such an orientation of an x1-y1-z1 coordinate system defined by the accuracy system is substantially fixed relative to the phantom base. Hence, the accuracy system may be configured such that, when the accuracy system mechanically engages the phantom base, the accuracy system may substantially map the x1-y1-z1 coordinate system defined by the accuracy system to the x-y-z coordinate system defined by the stereotactic system.

In some examples, the accuracy system defines one or more visible indicia defining a distance in the x1 direction, the y1 direction, and/or the z1 direction of x1-y1-z1 coordinate system defined by the accuracy system. The accuracy system may be configured such that, when the accuracy system mechanically engages a phantom base and the phantom base mechanically engages a stereotactic system, the visible indicia of the accuracy system may define the displacement between a target point and a pointer tip. For example, the visible indicia may define the displacement in one or more of a direction parallel to the x1 axis, a direction parallel to the y1 axis, and a direction parallel to the z1 axis. The accuracy system may thus provide an output indicating an x displacement, a y displacement, and/or a z displacement to a practitioner using the visible indicia. The accuracy system may be configured to mechanically engage an individual pin of the phantom base to determine a displacement between a pointer tip and the target point defined by the individual pin. The accuracy system may be configured such that a practitioner may mechanically engage and mechanically disengage the accuracy system and the individual pin, such that the practitioner may transfer the accuracy system from a first pin to a second pin to determine the displacement between a pointer tip and each of the target points defined by a plurality of pins.

In some examples, the accuracy system is configured to define a displacement between a pointer tip and a target point defined by the phantom base using two or more images of the pointer tip and the target point. The accuracy system may include a first camera and a second camera and processing circuitry configured to receive a first image from the first camera and a second image from the second camera. The accuracy system may be configured to mechanically engage the phantom base such that the processing circuitry may define a location of the first camera relative to a target point and a location of the second camera relative to the target point. The processing circuitry may be configured to substantially recognize (e.g., using imaging recognition software) the target point defined by the phantom base and the pointer tip of the stereotactic system in the first image and in the second image. The processing circuitry may be configured to determine an x displacement, a y displacement, and/or a z displacement between the target point and the pointer tip by substantially comparing the first image and the second image. For example, the processing circuitry may be configured be configured to establish a imaged locations of the target point and the pointer tip in the first image using an image coordinate system of the first camera and establish a imaged locations of the target point and the pointer tip in the second image using an image coordinate system of the second camera. The processing circuitry may be configured to determine the x displacement, the y displacement, and/or the z displacement using the image coordinate systems and the spatial relationship between the first camera, the second camera, and the phantom base. The accuracy system may thus provide an output to a display indicating the x displacement, a y displacement, and/or a z displacement to a practitioner.

In examples, the accuracy system may include a probe tip configured to mechanically engage with the pointer of the stereotactic system to assist the first camera, second camera, and/or the processing circuitry in identification of the pointer tip. The probe tip may include, for example, reflective paint and/or markings configured to assist the first camera, second camera, and/or processing circuitry in identification of the pointer tip. In examples, the probe tip is configured to mechanically engage the pointer to establish a substantially fixed position with respect to the pointer tip. In some examples, the probe tip defines the pointer tip. In some examples, the accuracy system may include and/or be configured to utilize a reflective paint or markings on one or more pins of the phantom base to assist the first camera, second camera, and/or processing circuitry in identification of the pointer tip and/or a target point.

FIG. 1 is a conceptual diagram illustrating an example accuracy system 100 configured to determine a displacement D between a target point 102 defined by a phantom base 104 and a pointer tip 106 of a stereotactic system 108. Stereotactic system 108 includes pointer 110 defining pointer tip 106. Phantom base includes pin 112 defining target point 102. Phantom base 104 is mechanically engaged with stereotactic system 108 such that target point 102 is substantially stationary relative to stereotactic system 108. Stereotactic system 108 is configured to cause a translation of pointer 110 to position pointer tip 106 at locations within a volume V defined by stereotactic system 108. The volume V may be defined by range of translations of pointer tip 106 enabled by stereotactic system 108. In examples, stereotactic system 108 enables translations of pointer tip 106 within an x-y-z coordinate system defined by stereotactic system 108.

Stereotactic system 108 may include a stereotactic frame 118 configured to fixedly attach to the head of a patient and position relative to the head of the patient. Stereotactic frame 118 may be, for example, a rigid stereotactic frame, a mini-frame, a frameless delivery device, image/MRI guided/navigated accuracy system, patient specific 3D printed device, or some other accuracy system configured to provide positional reference relative to a patient. While illustrated in FIG. 1 as using stereotactic system 108, accuracy system 100 may be used without stereotactic system 108, or may be used with other apparatus, pointing or aiming devices with or without tool holders, translocation methods, guidance, and/or placement accuracy systems in other examples.

Stereotactic frame 118 may include a head frame 119 configured to engage the head of the patient. Head frame 119 may be configured to remain substantially stationary with the head of the patient when head frame 119 engages the head of the patient. In examples, head frame 119 is mechanically engaged with stereotactic frame 118. Stereotactic frame 118 may be configured to allow the translation of pointer 110 to translate pointer tip 106 relative to head frame 119, such that stereotactic system 108 may position pointer tip 106 within an intercranial space of the patient when head frame 119 engages the patient. In examples, stereotactic system 108 defines the x-y-z coordinate system such that the x-y-z coordinate system is stationary with respect to at least portion of head frame 119. The x axis or the y axis of the x-y-z coordinate system may be representative of a horizontal anatomical plane of a patient The z axis of the x-y-z coordinate system may be representative of a medial anatomical plane or a coronal anatomical plane of a patient. In examples, the x-y-z coordinate system defines one or more locations in an intercranial space of a patient, and one of the x displacement or the y displacement is substantially parallel to an anterior or posterior direction of the patient and the other of the x displacement or the y displacement is substantially parallel to a left lateral or a right lateral direction of the patient. The z displacement may be substantially parallel to a superior or inferior direction of the patient.

Stereotactic system 108 may be configured to translate one or more translatable components of stereotactic frame 118 relative to head frame 119 to position pointer tip 106 within the volume V. For example, stereotactic system 108 may be configured to translate a frame member 122, a mount 120, and/or a carrier platform 128 relative to head frame 119 to position pointer tip 106. In examples, stereotactic system 108 is configured to translate the one or more translatable components relative to a fixed point P of head frame 119. Stereotactic system 108 may be configured translate a translatable component of stereotactic frame 118 in any direction described by an x-y-z coordinate system defined by stereotactic system 108 to position pointer tip 106 within volume V. An x-y-z coordinate system defined by stereotactic system 108 is represented by the x axis, the y axis, and the z axis of FIG. 1, wherein the x axis proceeds out of the page.

Stereotactic system 108 may define the x-y-z coordinate system such that the x axis, the y axis, and the z axis have a fixed orientation relative to head frame 119 or some other portion of stereotactic system 108. Stereotactic system 108 may be configured to translate a translatable component relative to head frame 119 in one or more linear directions parallel to the x axis, the y axis, and/or the z axis to position pointer tip within the volume V. Stereotactic system 108 may be configured to translate a translatable component relative to head frame 119 in one or more rotational directions around the x axis, the y axis, and/or the z axis to position pointer tip within the volume V. In examples, stereotactic system 108 is configured such that a mechanical engagement among the one or more translatable components enable pointer tip 106 to be positioned substantially at any point within volume V using the linear and/or rotational translations of the one or more translatable components relative to head frame 119. Further, although represented as a set of orthogonal axis in FIG. 1 for illustration, stereotactic system 108 may define the x-y-z coordinate system using any coordinate system sufficient to define a three-dimensional location within interior volume V, including a cartesian coordinate system, a polar coordinate system, a spherical coordinate system, any combinations thereof, or any other coordinate system.

As an example, stereotactic frame 118 may be configured such that frame member 122 may rotationally translate relative to head frame 119 around a pivot axis 124 of stereotactic system 108, using, for example, arc supports 126. Stereotactic frame 118 may include a mount 120 (e.g., an instrument stop/guide holder) mechanically supported by frame member 122 and configured to translate relative to frame member 122. Mount 120 may be configured to support pointer 110 and/or other components of stereotactic system 108. In examples, frame member 122 defines a substantially semicircular arc along which mount 120 may be adjustably positioned. Hence, in the example of FIG. 1, mount 20 may be positioned at various points on a spherical dome defined by the rotation of frame member 122 relative to head frame 119.

Pointer 110 may be configured to mechanically couple with mount 120 such that a displacement of mount 120 relative to head frame 119 causes a displacement of pointer 110 and pointer tip 106 relative to head frame 119. In examples, pointer 110 is configured to engage a carrier platform 128 mechanically coupled to mount 120. Carrier platform 128 may be configured to translate (e.g., along an axis A) relative to mount 120. In some examples, translation of carrier platform 128 (and pointer 110 when engaged) relative to mount 120 may be at least partially automated with the use of an optional drive member, such as drive motor 130 (e.g., operated manually or using an electric motor). Drive motor 130 may be configured to selectively advance or withdraw carrier platform 128 and pointer 110 along an axis A relative to mount 120. In an example, translation of carrier platform 128 along the axis A causes translation of pointer 110 and pointer tip 106 along the axis A. Thus, the configuration of stereotactic frame 118 allowing mount 20 to position on a spherical dome defined by the rotation of frame member 122 and allowing pointer 110 to translate along the axis A enables the placement of pointer tip 106 at specific points within the volume V defined by stereotactic system 108. When head frame 119 engages the head of a patient, stereotactic frame 118 may enable pointer tip 106 to be positioned at points within an intercranial space of the patient.

Stereotactic system 108 may be configured such that one or more of the translatable components (e.g., frame member 122, mount 120) may be manually positioned by a practitioner in order to, for example, place stereotactic frame in a specific orientation causing pointer tip 106 to position at a specific location within the volume V. In examples, stereotactic system 108 includes one or more indexing indications to indicate when stereotactic system 108 has established the specific orientation. For example, stereotactic system 108 may include angle markers 132 configured to indicate an orientation of mount 120 relative to frame member 122. Stereotactic system 108 may include position markers configured to indicate an orientation of frame member 122 relative to head frame 119 (e.g., position markers associated with arc supports 126). The indexing indications may thus be configured to indicate an orientation of the one or more translatable components relative to head frame 119, such that a practitioner may recognize when stereotactic frame 118 is in a specific configuration corresponding to a specific location of pointer tip 106 within the volume V.

In some examples, instead of or in addition to manual positioning by a practitioner, stereotactic system 108 may include circuitry 134 configured to cause stereotactic frame 118 to translate one or more translatable components and establish a specific orientation. For example, circuitry 134 may be configured to communicate with stereotactic frame 118 (e.g., drive motor 130) via communication link 136 to cause stereotactic frame 118 to translate carrier platform 128 and/or pointer 110 relative to head frame 119 (e.g., along axis A). Circuitry 134 may be configured to communicate with stereotactic frame 118 to cause stereotactic frame 118 to translate frame member 122 and/or mount 120 relative to head frame 119 (e.g., using one or more servomotors). In examples, circuitry 134 may be configured to receive an input from input device 138 (e.g., via communication link 140) specifying a specific orientation of stereotactic frame 118 and/or a position of pointer tip 106 within volume V and issue communications to stereotactic frame 118 based on the input. Stereotactic frame 118 may be configured to position the one or more translatable components based on the communication received by circuitry 134.

Hence, stereotactic system 108 may be configured such that a position of pointer tip 106 within the volume V is substantially determined based on an orientation of one or more translatable components (e.g., frame member 122, mount 120, and/or carrier platform 128) of stereotactic frame 118 relative to volume V. Stereotactic system 108 may be configured to establish a specific orientation (e.g., by manual positioning by a practitioner and/or using circuitry 134) intended to position pointer tip 106 at a specific location within volume V. Thus, stereotactic system 108 may be configured such that specific orientations of stereotactic system 108 correspond to specific locations of pointer tip 106 within volume V. Stereotactic system 108 may be configured to treat the specific configuration established as a proxy for the specific location of pointer tip 106. However, due to misalignments, hysteresis, wear, or other mechanical or control system effects, an actual, real-space location of pointer tip 106 within interior volume V may differ from the specific location of pointer tip 106 corresponding to the specific orientation establish by stereotactic system 108. This may introduce positional errors when stereotactic system 108 is utilized to position pointer tip 106 within an intercranial space of a patient engaged by head frame 119.

Phantom base 104 is configured to engage stereotactic system 108 to define one or more target points such as target point 102 within the volume V. In examples, phantom base 104 is configured to mechanically engage head frame 119 of stereotactic system 108. Phantom base 104 is configured to define target point 102 at a known, real-space location within the x-y-z coordinate system defined by stereotactic system 108 when phantom base 104 engages stereotactic system 108. In examples, pin 112 of phantom base 104 defines target point 102. In some examples, phantom base 104 includes a plurality of pins defining a plurality of target points, such as pin 112 defining target point 102 and pin 142 defining target point 144. Pins 112, 142 extending from first end secured to a support plate 146 of phantom base 104 to a second end defining target points 102, 144. Phantom base 104 may be configured to engage stereotactic system 108 such that target points 102, 144 are substantially stationary relative to the x-y-z coordinate system defined by stereotactic system 108, such that target points 102, 144 define substantially stationary real-space locations within interior volume V. In examples, phantom base 104 is configured to engage stereotactic system 108 such that target points 102, 144 are substantially stationary relative to a fixed point P of head frame 119.

Phantom base 104 may be configured (e.g., dimensioned) such that, when phantom base 104 engages stereotactic system 108 (e.g., head frame 119), target points 102, 144 define specific real-space locations defined by the x-y-z coordinate system of stereotactic system 108. The specific real-space locations defined by the x-y-z coordinate system may be known to a practitioner based on, for example, manufacturing specifications for phantom base 104, measurement relative to a portion of head frame 119 (e.g., fixed point P), or by some other method. Hence, a practitioner may utilize phantom base 104 to establish target points 102, 144 at specific, real-space locations defined by the x-y-z coordinate system within volume V when phantom base 104 engages stereotactic system 108. Phantom base 104 may be used to indicate a positioning error of stereotactic system 108 by causing stereotactic system 108 (e.g., manually and/or with circuitry 134) to establish a specific configuration corresponding to a real-space location defined by one of target point 102 or target point 144. A displacement between target point 102, 144 and a location of pointer tip 106 with stereotactic system 108 in the specific orientation is indicative of the positioning error.

Accuracy system 100 is configured to determine the accuracy of stereotactic system 108 when stereotactic system 108 establishes a specific orientation corresponding to a real-space location defined by target point 102 (or target point 144). Accuracy system 100 is configured to determine (e.g., quantify) the displacement D between pointer tip 106 as positioned by stereotactic system 108 and target point 102 when stereotactic system 108 establishes the specific orientation. Accuracy system 100 is configured to determine the displacement based on a spatial comparison of target point 102 the location of pointer tip 106 within volume V when an output of stereotactic system 108 (e.g., angle markers 132, other poisoning indexes, or circuitry 134) indicates stereotactic system 108 is in the specific orientation necessary to place pointer tip 106 at target point 102. The spatial comparison serves to indicate the magnitude and the associated directions of the error of stereotactic system 108, such that a practitioner may be informed of the placement accuracy of stereotactic system 108. Accuracy system 100 may be configured to define the spatial relationship between pointer tip 106 and the target point 102 and provide an output viewable by the practitioner. In examples, accuracy system 100 includes visible indicia indicating the displacement D between pointer tip 106 and target point 102, such that the practitioner may observe the visible indicia as an indication of the displacement. In examples, accuracy system 100 defines the spatial relationship and determines one or more magnitudes and/or one or more directions describing the displacement D and provides the magnitudes and/or directions to a display viewable by the practitioner.

Accuracy system 100 is configured to define the displacement D in an x-direction, a y-direction, and/or a z-direction. The x-direction, the y-direction, and/or the z-direction may be directions defined by the x-y-z coordinate system of the stereotactic system 108. In some examples, accuracy system 100 is configured to define the displacement D using an x1 axis, a y1 axis, and/or a z1 axis of an x1-y1-z1 coordinate system defined by accuracy system 100 and substantially map the displacement D to the x-y-z coordinate system of stereotactic system 108, such that the output informs the practitioner of the accuracy using the x-y-z coordinate system of the stereotactic system 108.

In examples, stereotactic frame 108 and/or accuracy system 100 includes an accuracy finder 141 configured to determine a distance from pointer tip 106 to a target point such as target point 102, 144. Accuracy finder 141 may be configured to be supported (e.g., mechanically supported by some portion of stereotactic system 108, such as carrier platform 128 and/or mount 120. In examples, accuracy finder 141 is configured to remain substantially stationary relative to the portion of stereotactic system 108 (e.g., carrier platform 128 and/or mount 120). Accuracy finder 141 may be configured to be substantially portable relative to stereotactic frame 108 such that, for example, a user may attach accuracy finder 141 to stereotactic frame 108 and/or remove accuracy finder 141 from stereotactic frame 108. For example, accuracy finder 141 may be configured to be attached to and/or removed from a frame adapter supported by stereotactic system 108.

Accuracy finder 141 may be configured to determine and/or assist accuracy system 100 in determining a displacement (e.g., the displacement D) between pointer tip 106 as positioned by stereotactic system 108 and target point 102, 144. For example, a user may set stereotactic system 108 such that stereotactic system 108 establishes a specific orientation corresponding to a real-space location defined by target point 102, 144. In examples, accuracy finder 141 may be set to a frame arc radius of stereotactic frame 108. The user may set accuracy finder 141 to frame a specific orientation (e.g., lateral left, lateral right), such that accuracy finder 141 may determine directions such as anterior, posterior, left, right. The user may set accuracy finder 141 for a certain hemisphere, such that accuracy finder 141 may determine directions such as medial and lateral. The accuracy finder may be configured to locate phantom tip 106. If phantom tip 106 is not aligned with accuracy finder 141, accuracy finder 141 may determine the displacement between target point 102, 144. For example, accuracy finder 141 may determine the displacement by determining a number of degrees by which pointer tip 106 is separated from target point 102, 144. In examples, accuracy system 141 includes a range finder configured to determine a range to target pointer tip 106. Accuracy system 141 may be configured use the number of degrees, the range, and/or another measure to determine a distance and/or a direction (e.g., anterior, posterior, medial, lateral) indicative of the separation between pointer tip 106 and target point 102, 144. Accuracy finder 141 may be an example of accuracy system 100 and/or may be utilized in addition to accuracy system 100.

Accuracy system 141 may include processing circuitry configured to determine the displacement D in an x1 axis, a y1 axis, and/or a z1 axis of an x1-y1-z1 coordinate system using the range the pointer tip 106, the number of degrees by which pointer tip 106 is separated from target point 102, 144, and/or another measure. The processing circuitry of accuracy system 141 may be configured to substantially map the x1-y1-z1 coordinate system to the x-y-z coordinate system of stereotactic system 108 to determine a displacement D. Accuracy finder 141 may be an example of accuracy system 100 and/or may be utilized in addition to accuracy system 100.

FIG. 1 illustrates an example x1-y1-z1 coordinate system defined by accuracy system 100, with the x1 axis proceeding out of the page. In the example of FIG. 1, the x1-y1-z1 coordinate system defined by accuracy system 100 is oriented similarly to the x-y-z coordinate system defined by stereotactic system 108, however this is not required. Further, although represented as a set of orthogonal axis in FIG. 1 for illustration, accuracy system 100 may define the x1-y1-z1 coordinate system using any coordinate system sufficient to define a three-dimensional location within interior volume V, including a cartesian coordinate system, a polar coordinate system, a spherical coordinate system, any combinations thereof, or any other coordinate system. Accuracy system 100 may be configured to map the x1-y1-z1 coordinate system to the x-y-z coordinate system for any orientation of the x1-y1-z1 coordinate system relative to the x-y-z coordinate system.

In examples, accuracy system 100 is configured to mechanically engage some portion of phantom base 104 to define the displacement D. In examples, accuracy system 100 is configured such that at least some portion of accuracy system 100 is substantially stationary relative to phantom base 104 when accuracy system 100 mechanically engages phantom base 104. In examples, accuracy system 100 is configured to mechanically engage phantom base 104 such an orientation of the x1-y1-z1 coordinate system is substantially fixed relative to phantom base 104. Hence, accuracy system 100 may be configured such that, when accuracy system 100 mechanically engages phantom base 104 and phantom base 104 mechanically engages stereotactic system 108, accuracy system 100 may substantially map the x1-y1-z1 coordinate system to the x-y-z coordinate system of stereotactic system 108.

Accuracy system 100 is configured to define the spatial relationship between pointer tip 106 and target point 102 and provide an output indicative of the spatial relationship. In examples, accuracy system 100 defines one or more visible indicia defining a distance in the x1 direction, the y1 direction, and/or the z1 direction of x1-y1-z1 coordinate system to define the displacement D and provide the output. In some examples, accuracy system 100 is configured to define the displacement D using two or more images of pointer tip 106 and target point 102 and communicate the displacement D to a display to provide the output.

Figure 2:
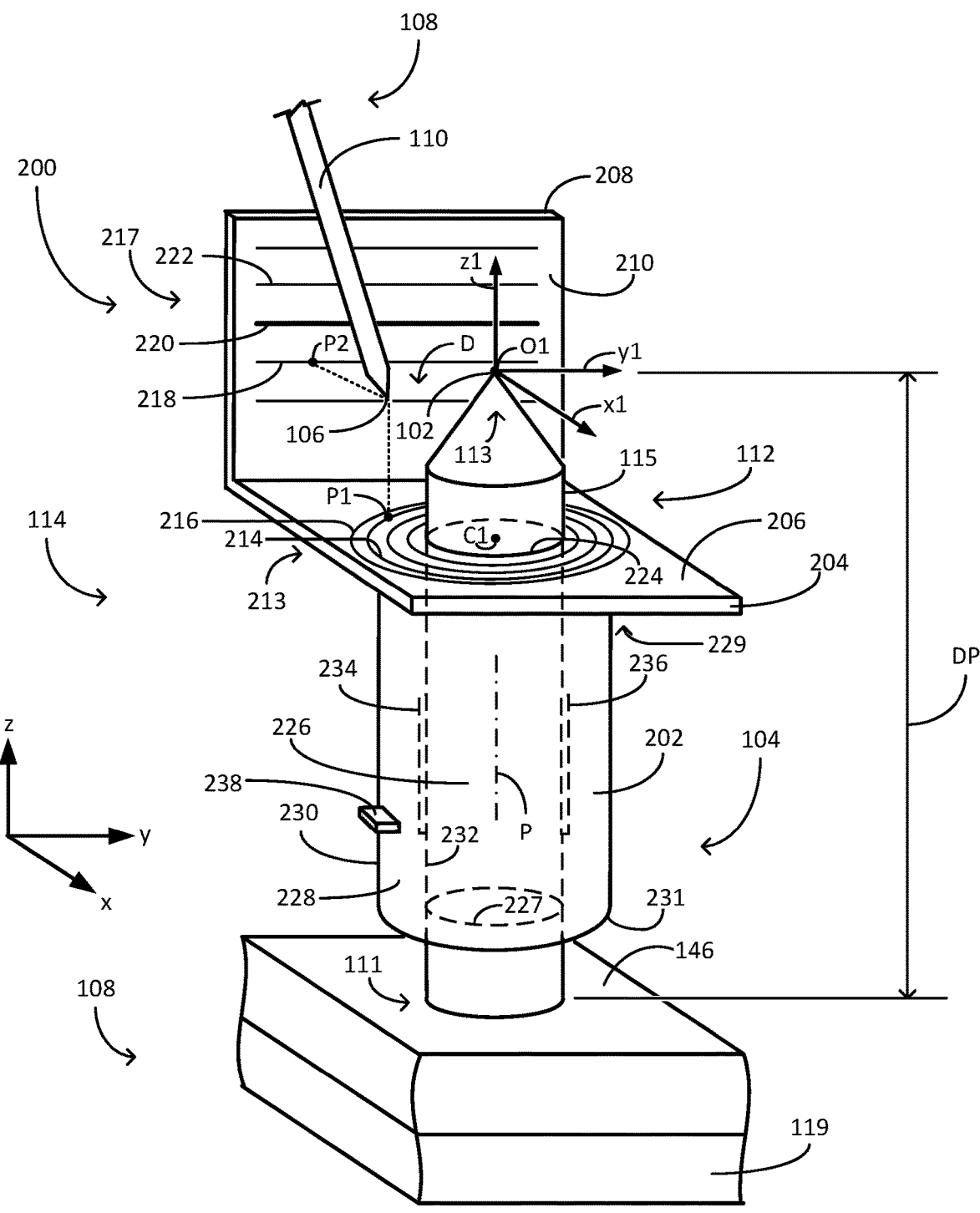
FIG. 2 is an isometric view illustrating an example accuracy system configured to determine a displacement D between a pointer tip and a target point.
Figure 3B:
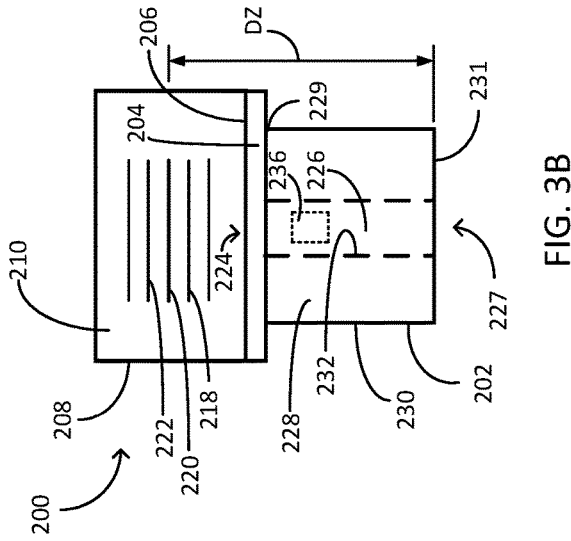
FIG. 3B is a side view of the example accuracy system of FIG. 2 and FIG. 3A.
Figure 3C:
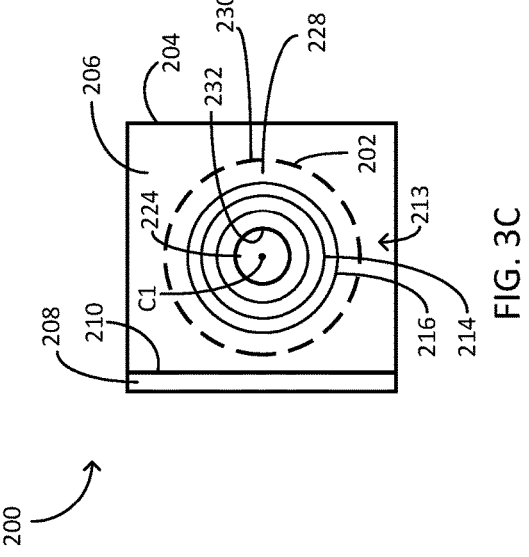
FIG. 3C is a top view of the example accuracy system of FIGS. 2, 3A, and 3B.
Figure 3A:
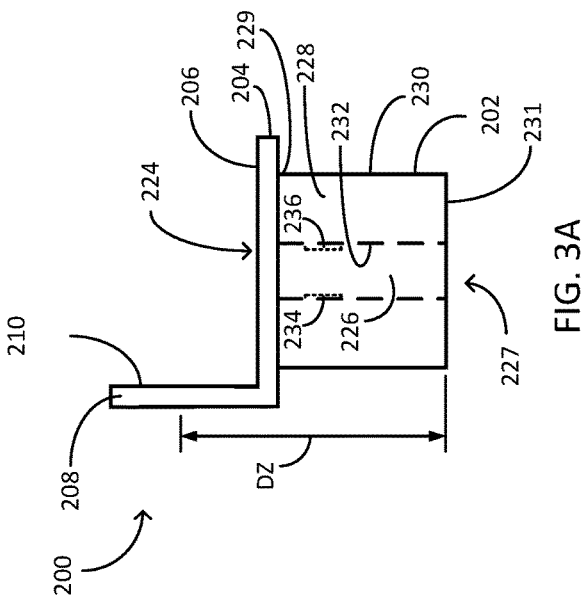
FIG. 3A is a side view of the example accuracy system of FIG. 2.

FIG. 2 illustrates an accuracy system 200 configured to determine an accuracy of a stereotactic system 108 by determining the displacement D between target point 102 of phantom base 104 and pointer tip 106 of stereotactic system 108. Accuracy system 200 is an example of accuracy system 100. Phantom base 104 is mechanically engaged to stereotactic frame 118 such that target point 102 is substantially stationary relative to at least a portion of stereotactic frame 118 and the x-y-z coordinate system defined by stereotactic system 108. In examples, support plate 146 is mechanically engaged with head frame 119. The translatable components of stereotactic frame 118 (e.g., frame member 122, mount 120, carrier platform 128 (FIG. 1)) are positioned such that stereotactic frame 118 is in a specific orientation corresponding to the real-space location defined by target point 102. The specific orientation of stereotactic frame 118 causes pointer tip 106 to position in a location displaced from target point 102 by the displacement D. Accuracy system 200 may define an x1-y1-z1 coordinate system to define the displacement D. FIG. 3A, FIG. 3B. And FIG. 3C illustrate plan views of accuracy system 200, with FIG. 3A providing a side view projected onto an image plane parallel to plane defined by the x1 axis and the z1 axis of FIG. 2, FIG. 3B providing a side view projected onto an image plane parallel to plane defined by the y1 axis and the z1 axis of FIG. 2, and FIG.

3C providing a top view projected onto an image plane parallel to plane defined by the x1 axis and the y1 axis of FIG. 2.

Accuracy system 200 includes a gauge support 202 is configured to mechanically engage phantom base 104. Accuracy system 200 is configured such that accuracy system 200 defines the displacement D relative to target point 102 when gauge support 202 mechanically engages phantom base 104. In examples, gauge support 202 is configured to mechanically engage pin 112. Accuracy system 200 may be configured such that at least some portion of accuracy system 200 is substantially stable relative to phantom base 104 when gauge support 202 mechanically engages phantom base 104. Hence, accuracy system 200 may be configured to be substantially stationary relative to a portion of stereotactic frame 118 (e.g., head frame 119) when gauge support 202 mechanically engages phantom base 104 and phantom base 104 mechanically engages stereotactic system 108 (e.g., head frame 119). In examples, accuracy system 200 is configured to define an origin O1 of its x1-y1-z1 coordinate system substantially at target point 102 when the gauge support mechanically engages phantom base 104, although this is not required.

Gauge support 202 may be configured to mechanically engage pin 112. In examples, pin 112 may include a first end 111 ("pin first end 111") secured to support plate 146 and a second end 113 ("pin second end 113") opposite pin first end 111 and defining target point 102. In examples, pin 112 defines a displacement DP from pin first end 111 to pin second end 113. In examples, the displacement DP is substantially parallel to the z axis of the x-y-z coordinate system defined by stereotactic system 108. A pin body 115 defined by pin 112 may extend between pin first end 111 and pin second end 113 (e.g., over the displacement DP). Gauge support 202 may be configured to mechanically engage pin body 115. In examples, pin axis P extends through pin body 115 through pin first end 111 and pin second end 113.

Gauge support 202 may substantially surround at least a portion of pin body 115 and pin axis P when gauge support 202 may be configured to mechanically engage pin body 115. Gauge support 202 may substantially surround pin body over a portion of or substantially the entirety of the displacement DP. In FIG. 2, portions of pin body 115 at least partially surrounded by gauge support 202 are shown in dashed lines. Pin 112 may define target point 102 on some portion of pin second end 113. In examples, pin second end 113 defines an apex defining a maximum linear displacement from pin first end 111, and pin 112 defines target point 102 on pin second end 113 in the vicinity of the apex.

Accuracy system 200 is configured to determine an x displacement, a y displacement, and a z displacement describing the displacement D between pointer tip 106 and target point 102 when accuracy system 200 mechanically engages phantom base 104. The x displacement, the y displacement, and the z displacement may be vector components of a position vector extending between target point 102 and pointer tip 106. In examples, the x displacement is a distance along the x1 axis, the y displacement is a distance along the y1 axis, and the z displacement is a distance along the z1 axis. As previously discussed, although the x1-y1-z1 coordinate system is represented as a set of orthogonal axis in FIG. 2, accuracy system 200 may define the x1-y1-z1 coordinate system using any coordinate system sufficient to define a three-dimensional location within interior volume V, including a cartesian coordinate system, a polar coordinate system, a spherical coordinate system, any combinations thereof, or any other coordinate system.

In examples, accuracy system 200 includes a gauge base 204 mechanically supported by gauge support 202. Gauge base 204 may be configured to at least partially define the displacement D between target point 102 and pointer tip 106 when gauge support 202 mechanically engages pin. Gauge base 204 may define, for example, one or more of the x displacement and/or the y displacement between the target point and the pointer tip. In examples, gauge base 204 defines a surface 206 ("gauge base surface 206") configured to define the x1 axis and the y1 axis of the x1-y1-z1 coordinate system. Gauge base surface 206 may be a substantially planer surface which defines an x1-y1 plane including the x1 axis and the y1 axis. In examples, gauge base surface 206 is configured to define the x1 axis and the y1 axis such that the x1 axis and the y1 axis are substantially perpendicular. Accuracy system 200 may be configured such that, when gauge support 202 mechanically engages phantom base 104 (e.g., pin 112), gauge base 203 (e.g., gauge base surface 206) defines the x1 axis and the y1 axis substantially perpendicularly to the pin axis P extending through pin 112.

Accuracy system 200 may include a z-member 208 mechanically supported by gauge support 202. Z-member 208 may be configured to at least partially define the displacement D between target point 102 and pointer tip 106 when gauge support 202 mechanically engages pin 112. Z-member 208 may define, for example, the z displacement between the target point and the pointer tip. In examples, z-member 208 defines a surface 210 ("z-member surface 210") configured to define the z1 axis of the x1-y1-z1 coordinate system. Z-member surface 210 may be a substantially planer surface which substantially defines a plane that includes the z1 axis. In examples, z-member surface 210 is configured to define the z1 axis such that the z1 axis is substantially perpendicular to at least one of the x1 axis and the y1 axis. Accuracy system 200 may be configured such that z-member 208 (e.g., z-member surface 210) defines the z1 axis substantially parallel to the pin axis P when gauge support 202 mechanically engages phantom base 104 (e.g., pin 112).

Accuracy system 200 may be configured such that, when gauge support 202 mechanically engages pin 112 (e.g., pin body 115), accuracy system 200 establishes the z1 axis in a defined orientation (e.g., substantially parallel) relative to the pin axis P and establishes the x1-y1 plane in a defined orientation (e.g., substantially perpendicular) relative to pin axis P, such that when gauge support 202 mechanically engages pin 112, accuracy system 200 establishes the x1-y1-z1 coordinate system in a defined orientation relative to pin axis P. Phantom base 104 may be configured such that pin axis P has a defined orientation (e.g., substantially parallel) relative to a z axis or other axis defined by the x-y-z coordinate system of stereotactic system 108 when phantom base 104 (e.g., support plate 146) mechanically engages stereotactic system 108. Thus, in examples, accuracy system 200 is configured such that when gauge support 202 mechanically engages pin 112 of phantom base 104 and phantom base 104 is mechanically engaged with stereotactic system 108, accuracy system 200 substantially maps one or more axes of the x1-y1-z1 coordinate system defined by accuracy system 200 to the x-y-z coordinate system defined by stereotactic system 108.

As used herein, when a first line is substantially parallel to a second line or a plane, or vice-versa, this may mean the first line is within 20 degrees, within 10 degrees, within 5 degrees, or within 1 degree of parallelism with the second line or the plane. When the first line is substantially perpendicular to a second line or a plane, or vice-versa, this may mean the first line is within 20 degrees, within 10 degrees, within 5 degrees, or within 1 degree of perpendicularity with the second line or the plane. A real-space location or real-space target point may mean an actual, physical location of some portion of an object or a target point within a volume of three-dimensional space, such as a volume V defined by a stereotactic system.

Accuracy system 200 may be configured to define the z1-y1-z1 coordinate system such that the z1 axis intersects pin 112 (e.g., pin second end 113) when accuracy system 200 mechanically engages pin 112. In examples, gauge base 204 is configured to cause the z1 axis to intersect pin 112 when accuracy system 200 mechanically engages pin 112. Accuracy system 200 may be configured to cause pin axis P to intersect the x1-y1 plane defined by gauge base 204 when accuracy system 200 mechanically engages pin 112. Gauge base 204 may be configured to cause the intersection of the x1-y1 plane when accuracy system 200 mechanically engages pin 112. In examples, when gauge support 202 mechanically engages pin 112, gauge support 202 is configured to substantially align the x1-y1-z1 coordinate system with pin 112 such that the z1 axis intersects pin 112 and the x1-y1 plane is intersected by pin axis P. In examples, accuracy system is configured such that, when gauge support 202 mechanically engages pin 112, gauge support 202 may be translated (e.g., by a practitioner) relative to pin 112 to locate the origin O1 of the x1-y1-z1 coordinate system substantially at the target point 102.

Accuracy system 200 (e.g., gauge support 202) may be configured to align pin 112 such the x1 axis, the y1 axis, and the z1 axis each define a distance along the respective axes from a portion of pin 112 (e.g., target point 102) when gauge support 202 mechanically engages pin 112. In examples, accuracy system 200 includes one or more visible indicia configured to demarcate distance along the x1 axis, the y1 axis, and/or the z1 axis. For example, accuracy system 200 may include one or more x-y visible indicia 213 such as x-y indicia 214 and/or x-y indicia 216 with each individual x-y visible indicia indicating a distance from the origin O1 to the individual x-y visible indica (e.g., a distance over the x1-y1 plane defined by gauge base 204). Accuracy system 200 may include one or more z visible indicia 217 such as z indicia 218, z indica 220, and/or z indicia 222, with each individual z visible indicia indicating a distance from the origin O1 to the individual z visible indica (e.g., a z-distance over the z1 axis defined by z-member 208). Hence, when the gauge support mechanically engages a pin defining a target point, the x-y visible indicia 213 and/or the z visible indicia 217 may define an x displacement between target point 102 and pointer tip 106, a y displacement between target point 102 and pointer tip 106, and/or a z displacement between target point 102 and pointer tip 106. Accuracy system 200 may thus provide an output indicating the x displacement, the y displacement, and/or the z displacement to a practitioner using the x-y visible indicia 213 and/or the z visible indicia 217.

As an example, and as discussed, FIG. 2 illustrates phantom base 104 mechanically engaged with stereotactic system 108 and defining target point 102 in real-space within volume V defined by stereotactic system 108. Phantom base 104 is configured to establish target point 102 at a specific location defined by the x-y-z coordinate system of stereotactic system 108. The translatable components of stereotactic system 108 (e.g., frame member 122, mount 120, carrier platform 128 (FIG. 1)) are positioned such that stereotactic system 108 is in a specific orientation corresponding to the real-space location defined by target point 102. When stereotactic system 108 establishes the specific orientation, the specific orientation causes pointer tip 106 to position in a real-space location displaced from the real-space location of target point 102, as depicted in FIG. 2.

In FIG. 2, gauge support 202 mechanically engages pin 112 such that the origin O1 of the x1-y1-z1 coordinate system is substantially at the target point 102 defined by pin 112. The x-y visible indicia 213 (e.g., x-y indica 214, 216) demarcate distances along the x1 axis and the y1 axis from the origin O1. In examples, accuracy system 200 defines a center point C1 located on the z1 axis, and the x-y visible indicia 213 (e.g., x-y indica 214, 216) demarcate distances along the x1 axis and the y1 axis from the center point C1 to demarcate distances from the origin O1. In examples, gauge support 202 is configured to locate the center point within pin 112 when gauge support 202 mechanically engages pin 112. The z visible indicia 217 (e.g., z indica 218, 220, 222) demarcate distance along the z1 axis from the origin O1. Accuracy system 200 is configured such that a projection of the location of pointer tip 106 (e.g., a projection substantially parallel to the z1 axis) defines a point P1 on a surface (e.g., gauge base surface 206) defining x-y visible indicia 213. The x displacement and/or the y displacement of the point P1 from the origin O1 may be determined by the vicinity of the point P1 relative to the x-y visible indica 213. For example, at FIG. 2, the point P1 is in the vicinity of x-y indica 214, indicating that pointer tip 106 is displaced from origin O1 by the x displacement and the y displacement demarcated by x-y indicia 213. Accuracy system 200 may be configured such that a practitioner may visibly observe pointer tip location 106 and x-y visible indicia 213, such that x-y visible indicia 213 provide an output indicating the x displacement and the y displacement to the practitioner. Gauge support 202 may be configured to map the x1-y1-z1 coordinate system to the x-y-z coordinate of stereotactic system 108 (e.g., may be configured to substantially align the x1-y1-z1 coordinate system with the x-y-z coordinate system), such that x displacement and the y displacement determined using x-y visible indica 213 are indicative of a distance along the x axis and the y axis defined by stereotactic system 108.

As similarly depicted in FIG. 2, accuracy system 200 is configured such that a projection of the location of pointer tip 106 (e.g., a projection substantially parallel to the x1-y1 plane) defines a point P2 on a surface (e.g., z-member surface 210) defining z visible indicia 217. The z displacement of the point P2 from the origin O1 may be determined by the vicinity of the point P2 relative to the z visible indica 217. For example, at FIG. 2, the point P2 is in the vicinity of z indica 218, indicating that pointer tip 106 is displaced from origin O1 by the z displacement demarcated by z indicia 218. Accuracy system 200 may be configured such that a practitioner may visibly observe pointer tip location 106 and z visible indicia 217, such that the z visible indicia 217 provide an output indicating the z displacement to the practitioner. Gauge support 202 may be configured to map the x1-y1-z1 coordinate system to the x-y-z coordinate of stereotactic system 108 (e.g., may be configured to substantially align the x1-y1-z1 coordinate system with the x-y-z coordinate system), such that z displacement determined using z visible indica 217 are indicative of a distance along the z axis defined by stereotactic system 108.

In examples, x-y visible indicia 213 includes one or more concentric circles centered around the z1 axis. An individual circle may define a distance from the z1 axis to the individual circle (e.g., a distance in the x1-y1 plane defined by accuracy system 200). In examples, the individual circle is coplanar with the x1-y1 plane, such that each point on the circle describes an x-distance parallel to the x1 axis and a y-distance parallel to the y1 axis from the center of the circle. In other examples, x-y visible indicia 213 may define a substantially cartesian grid system (e.g., on gauge base surface 206). For example, x-y visible indicia 213 may define one or more lines substantially parallel to the x1 axis and one or more lines substantially parallel to the y1 axis which intersect at one or more locations to define points on the cartesian grid. The each defined point may describes a distance parallel to the x1 axis and a distance parallel to the y1 axis from the z1 axis.

Accuracy system 200 may be configured to translate (e.g., be translated by a practitioner) relative to pin 112 to reference the origin O1 of the x1-y1-z1 coordinate system to a specific visible indicia, such that the displacement D may be determined with reference to the specific visible indicia. In examples, accuracy system 200 is configured to translate along the z1 axis relative to pin 112 to reference the origin O1 to one of z visible indicia 217 (e.g., z indicia 220). Accuracy system 200 may be configured to establish a position relative to pin 112 such that the one of z visible indicia 217 is substantially coplaner with target point 102 in a plane substantially parallel to or coincident with the x1-y1 plane defined by accuracy system 200 to reference the origin O1. For example, at FIG. 2, accuracy system 200 is positioned relative to pin 112 such that target point 102 is coplaner with z indicia 220 in a plane substantially parallel to or coincident with the x1-y1 plane. Hence, the origin O1 is referenced to z indicia 220, such that the z-displacement of point P2 from the origin O1 may be determined by the a distance between the point P2 and z indicia 220.

In some examples, accuracy system 200 defines a z-altitude over a displacement DZ (FIG. 3A, FIG. 3B) configured to cause the origin O1 to reference to a specific visible indicia when accuracy system 200 mechanically engages pin 112. Accuracy system 200 may define the displacement DZ such that, when gauge lower end 231 contacts support plate 146, the displacement DZ causes the specific visible indicia (e.g., z indicia 220) to position coplaner with target point 102 in a plane substantially parallel to or coincident with the x1-y1 plane defined by accuracy system 200. Hence, accuracy system 200 may be configured the origin O1 may be referenced to the specific visible indicia using contact between gauge lower end 231 and support plate 146. This may reduce and/or eliminate a need to translate accuracy system 200 relative to pin 112 to reference the origin O1 to the specific visible indicia. In examples, accuracy system 200 includes a plurality of gauge supports configured similarly to gauge support 202, with each gauge support defining a specific displacement DZ corresponding to a specific pin of phantom base 104. An individual gauge support may define the specific displacement DZ such that an origin of a coordinate system defined by the individual gauge support references to a specific visible indicia of the individual gauge support when an end of the individual gauge support contacts support plate 146. The individual gauge support may define the specific displacement DZ such that a specific z indicia of the specific gauge support is substantially coplaner with a target point defined by the specific pin in a plane substantially parallel to or coincident with an x1-y1 plane defined by the individual gauge support. Hence, accuracy system 200 may include a set of gauge supports, with each gauge support configured for use with a specific pin of phantom base 104.

Accuracy system 200 may be configured to receive some portion of pin 112 when accuracy system 200 mechanically engages pin 112. In examples, accuracy system 200 defines a pin access 224 configured to allow some portion of pin 112 to pass therethrough when accuracy system 200 mechanically engages pin 112. Pin access 224 may substantially surround center point C1 defined by accuracy system 200. Accuracy system 200 may be configured such that the z1 axis defined by the x1-y1-z1 coordinate system of accuracy system 200 intersects pin access 224 when accuracy system 200 mechanically engages pin 112. In examples, gauge base surface 206 defines pin access 224. In examples, pin access 224 is configured to establish the z1 axis in an orientation substantially parallel to pin axis P when pin 112 passes through pin access 224. Pin access 224 may substantially conform to a perimeter of pin 112 substantially parallel to the x axis and the y axis of the x-y-z coordinate system defined by stereotactic system 108 when pin 112 passes through pin access 224.

Accuracy system 200 may define a gauge cavity 226 (e.g., a tubular cavity) configured to receive pin 112 when accuracy system 200 mechanically engages pin 112. Pin access 224 may open into gauge cavity 226, such that pin 112 may pass through gauge cavity 226 and pin access 224 when accuracy system 200 mechanically engages pin 112. In examples, gauge support 202 defines gauge cavity 226. Gauge support 202 may include a body 228 ("gauge support body 228") defining an exterior surface 230 ("support exterior surface 230") and an interior surface 232 ("support exterior surface 232") opposite support exterior surface 230. Gauge support 202 may be configured such that support interior surface 232 defines gauge cavity 226. Support interior surface 232 may be configured to substantially maintain accuracy system 200 stationary relative to pin 112 when accuracy system 200 mechanically engages pin 112. Gauge support body 228 may define gauge lower end 231 ("gauge lower end 231"). In examples, gauge support body 228 defines an upper end 229 ("gauge upper end 229") at an end of gauge support body 228 opposite gauge lower end 231. In examples, gauge upper end 229 mechanically supports gauge base 204.

In examples, accuracy system 200 (e.g., gauge support body 228) defines a lower access 227 ("gauge lower access 227") configured to allow some portion of pin 112 to pass therethrough when accuracy system 200 mechanically engages pin 112. Accuracy system 200 may define lower access 227 in gauge lower end 231 of gauge support body 228. Gauge lower access 227 may open into gauge cavity 226. In examples, accuracy system 200 is configured such that gauge lower access 227 may be translated relative to pin 112 (e.g., pin body 115) to cause pin second end 113 to pass through gauge lower access 227 and enter gauge cavity 226. Gauge cavity 226 may be configured such that the relative translation between gauge lower access 227 and pin 112 causes pin second end 113 to pass through gauge cavity 226 and exit pin access 224. Hence, in examples, accuracy system 200 is configured such that a practitioner may cause accuracy system 200 to mechanically engage pin 112 by causing (e.g., through manual manipulation of accuracy system 200) gauge lower access 227 to receive pin body 115 and subsequently translating lower access 227 relative to pin body 115 to cause pin body 115 to enter gauge cavity 226. The practitioner may continue the relative translation between gauge lower access 227 and pin body 115 to cause pin second end 113 to exit pin access 224.

Gauge cavity 226 may be configured to substantially center pin 112 such that when gauge support 202 mechanically engages pin 112, pin axis P is substantially parallel with to the z1 axis of accuracy system 200. Gauge cavity 226 may be configured to substantially center pin 112 such that a pin axis P passes through pin access 224 when gauge support 202 mechanically engages pin 112. In examples, gauge cavity 226 is configured to center pin 112 such that the z1 axis intersects pin second end 113. In examples, gauge cavity 226 is configured to center pin 112 to cause the z1 axis to substantially intersect target point 102 when gauge support 202 mechanically engages pin 112. In examples, Gauge cavity 226 may be configured to center pin 112 such that the x1 axis and/or the y1 axis establish a substantially fixed vertex angle with pin axis P when gauge support 202 mechanically engages pin 112. In some examples, gauge cavity 226 is configured to center pin 112 such that the x1 axis and/or the y1 axis establish a vertex angle of about 90 degrees with pin axis P when gauge support 202 mechanically engages pin 112, such that the x1 axis and/or y1 axis are substantially perpendicular to pin axis P. In examples, gauge cavity 226 is configured such that, when gauge support 202 mechanically engages pin 112, gauge cavity 226 allows translation (e.g., sliding translation) of gauge support body 228 relative to pin 112. Gauge cavity 226 may be configured to allow the translation to, for example, allow a practitioner to translate gauge support body 228 to cause the origin O1 of the x1-y1-z1 coordinate system to position substantially at the target point 102.

Gauge support 202 may be configured to substantially grip a portion of pin body 115 when gauge support 202 mechanically engages pin 112. Gauge support 202 may be configured such that the gripping force causes gauge support 202 to remain substantially stationary with respect to pin 112. In examples, gauge support 202 defines one or more grip elements such as grip element 234 and grip element 236 configured to engage pin body 115 when gauge support 202 mechanically engages pin 112. Grip element 234, 236 may be configured to contact pin body 115 when gauge cavity 226 receives a portion of pin body 115. In examples, grip element 234, 236 is configured to frictionally engage pin body 115, such that translation of gauge support 202 relative to pin body 115 requires exertion of a force (e.g., by a practitioner) overcoming the gripping force. In some examples, grip element 234, 236 may be configured to frictionally engage pin body 115 to cause a gripping force on pin body 115 equal to or greater than a weight of accuracy system 200, such that when gauge cavity 226 receives pin body 115, grip element 234, 236 maintains gauge support 202 substantially stationary with respect to pin body 115 until an external force (e.g., exerted by a practitioner on gauge support 202) causes gauge support 202 to translate relative to pin body 115.

Grip element 234, 236 may be configured to grip pin body 115 in any manner sufficient to cause the gripping force on pin body 115. Grip element 234, 236 may be configured such that pin body 115 substantially compresses grip element 234, 236 when gauge cavity 226 receives pin body 115. For example, grip element 234, 236 may be configured to substantially protrude from support interior surface 232 in the absence of contact with an object such as pin body 115 within gauge cavity 226. Grip element 234, 236 may be configured to compress (e.g., toward support exterior surface 230) when the object such as pin body 115 contacts grip element 234, 236 within gauge cavity 226. In some examples, grip element 234, 236 is configured to form a snap fit, an interference fit, or some other fit with pin body 115 to cause the gripping force on pin body 115. In examples, grip element 234, 236 defines a recess configured to receive a protrusion defined by pin body 115 when gauge cavity 226 receives pin body 115. In some examples, one of grip element 234, 236 or pin body 115 defines a protrusion and the other of grip element 234, 236 or pin body 115 defines a recess configured to receive the protrusion when gauge cavity 226 receives pin body 115.

In some examples, grip element 234, 236 is configured to exert an inward clamping force (e.g., a force toward pin axis P) on pin body 115 to cause the gripping force on pin body 115. Grip element 234, 236 may be configured to exert the inward clamping force when gauge cavity 226 receives pin body 115. In some examples, accuracy system 200 includes a clamping mechanism 238 configured to cause grip element 234, 236 to exert the inward clamping force on pin body 115. In examples, clamping mechanism 238 is a movable component configured to cause grip element 234, 236 to exert the inward clamping force when clamping mechanism 238 is moved (e.g., by a practitioner) relative to gauge support 202. Clamping mechanism 238 may be, for example, a lever, a thumbscrew, or some other mechanism configured to cause grip element 234, 236 to exert the inward clamping force. In some examples, clamping mechanism 238 comprises a first section and a second section separable from the first section. The first section and the second section may be configured to mechanically mate to form a substantially unified portion of clamping mechanism 238. Clamping mechanism 238 may be configured such that mechanically mating the first portion and the second portion causes grip elements 234, 236 to exert the inward clamping force on pin body 115. The first component and the second component may comprise, for example, a stud and a socket (e.g., a snap fastener), a latch and a catch, a barrel bolt and a catch plate, or any other components configured to form a mechanically mated connection with each other. In some examples, clamping mechanism 238 may be configured to decrease the inward clamping force exerted by grip element 234, 236 on pin body 115 when clamping mechanism 238 is moved (e.g., by a practitioner) relative to gauge support 202 to, for example, allow the removal of gauge support 202 from pin 112 or the further translation of gauge support 202 with respect to pin 112.

Hence, accuracy system 200 is configured to determine the accuracy of stereotactic system 108 by defining a displacement D between pointer tip 106 positioned by stereotactic system 108 and target point 102, 144 defined by phantom base 104. Accuracy system 200 is configured to determine the displacement D based on a spatial comparison of the real-space target point (e.g., target point 102, 144) defined by phantom base 104 and an actual location of pointer tip 106 achieved when an output of stereotactic system 108 indicates pointer tip 106 is located at the real-space target point. The displacement D serves to indicate the magnitude and the associated directions of the indication error of stereotactic system 108, such that a practitioner may be informed of the placement accuracy of stereotactic system 108 when stereotactic system 108 attempts to achieve a specific coordinate.

Figure 4:
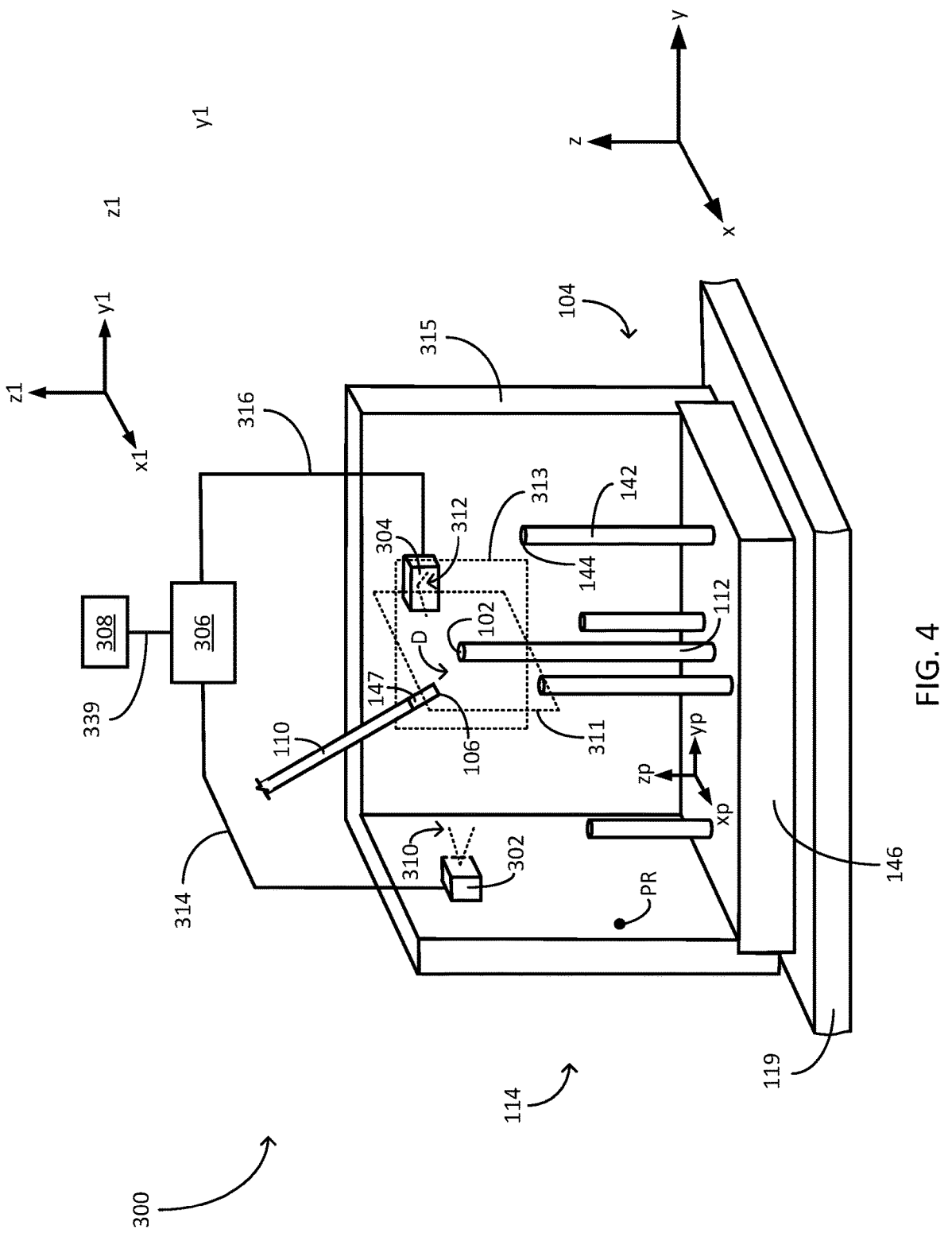
FIG. 4 is an isometric view illustrating an example accuracy system configured to determine the displacement D using a first camera and a second camera.

FIG. 4 illustrates an accuracy system 300 configured to determine an accuracy of a stereotactic system 108 using two or more images of target point 102 and pointer tip 106. Accuracy system 300 is an example of accuracy system 100. Accuracy system 300 includes one or more cameras configured to capture at least a first image of target point 102 and pointer tip 106 and a second image of target point 102 and pointer tip 106. The first image is captured using a field-of-view different from a field-of-view used to capture the second image, such that the first image and the second image generate a parallax between the apparent positions of target point 102 and pointer tip 106 in the first image compared with the second image. Accuracy system 300 includes processing circuitry 306 configured to determine the displacement D between target point 102 and pointer tip 106 by comparing the first image and the second image. Processing circuitry 306 may be configured to provide an output to a display 308 viewable by a practitioner indicating the displacement D. Accuracy system 300 may be configured to mechanically engage phantom base 104 to determine the displacement D.

Accuracy system includes one or more cameras configured to generate the first image and the second image. In some examples, the one or more cameras includes a first camera configured to generate the first image and a second camera configured to generate the second image. In other examples, the one or more cameras may be a single camera configured to generate the first image from a first location and separately generate the second image from a second location different from the first location. Hence, although FIG. 4 represents the one or more cameras as a first camera 302 and a second camera 304 for illustrative clarity, accuracy system 300 may generate the first image and the second image using a single camera or a plurality of cameras. Thus, when this disclosure and the examples provided herein refer to a first camera 302, this may refer to an individual camera positioned to generate a first image in the same manner as that described for first camera 302. When this disclosure and the examples provided herein refer to a second camera 304, this may refer to another camera distinct from the individual camera, or may refer to the individual camera positioned to generate a second image in the same manner as that described for second camera 304.

Figure 5:
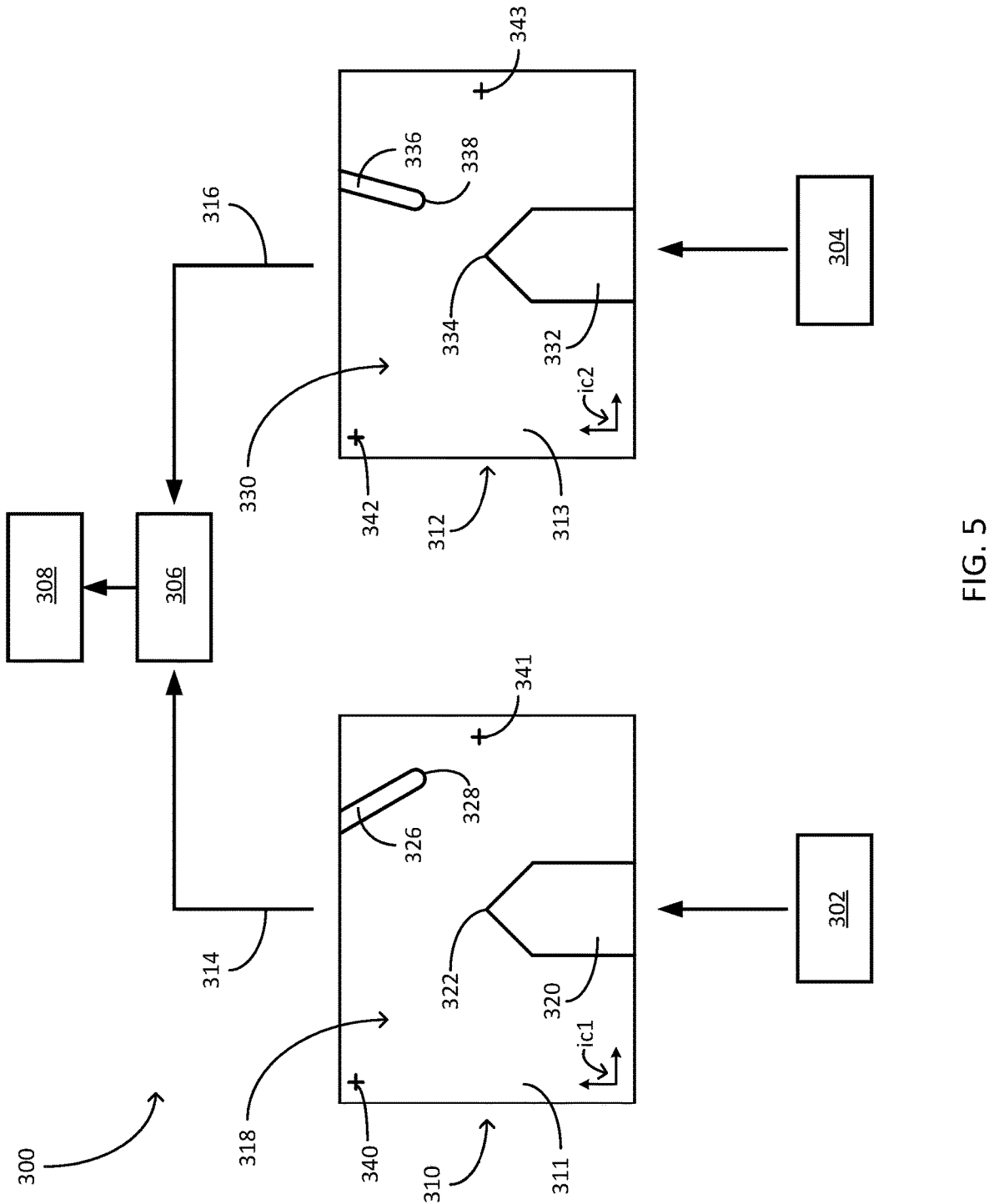
FIG. 5 is an example flow chart illustrating example operations of the accuracy system of FIG. 4.
Figure 6:
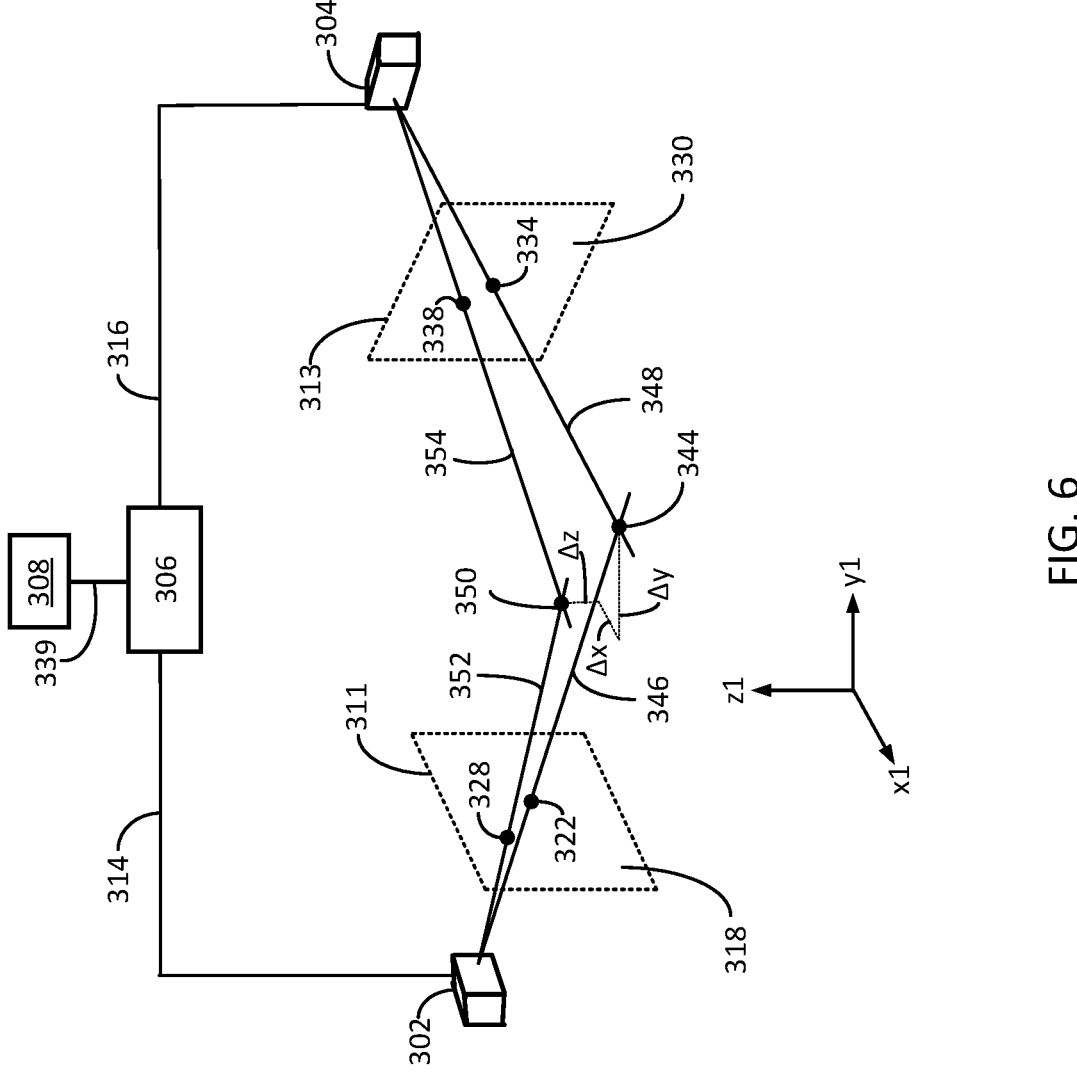
FIG. 6 is an isometric view illustrating the example accuracy system of FIG. 4 and FIG. 5 defining a representative location of a pointer tip and a target point.
Figure 6:
Figure 7A:
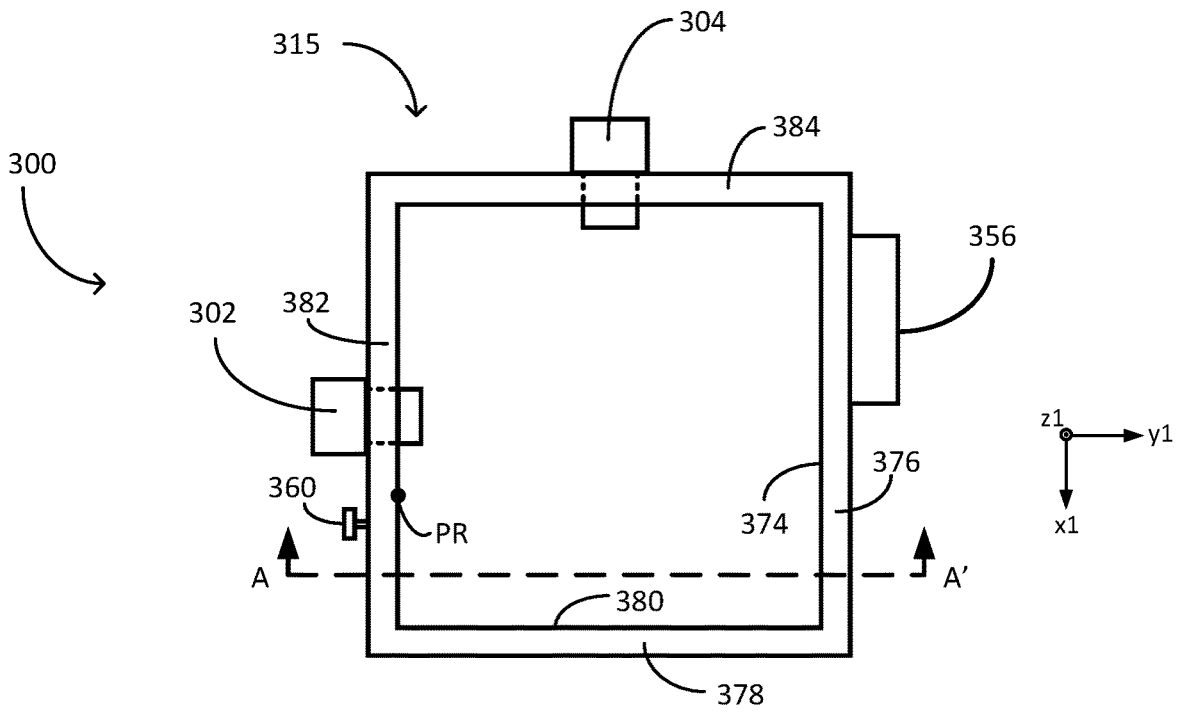
FIG. 7A is a plan view illustrating the example accuracy system of FIGS. 4-6.
Figure 7B:
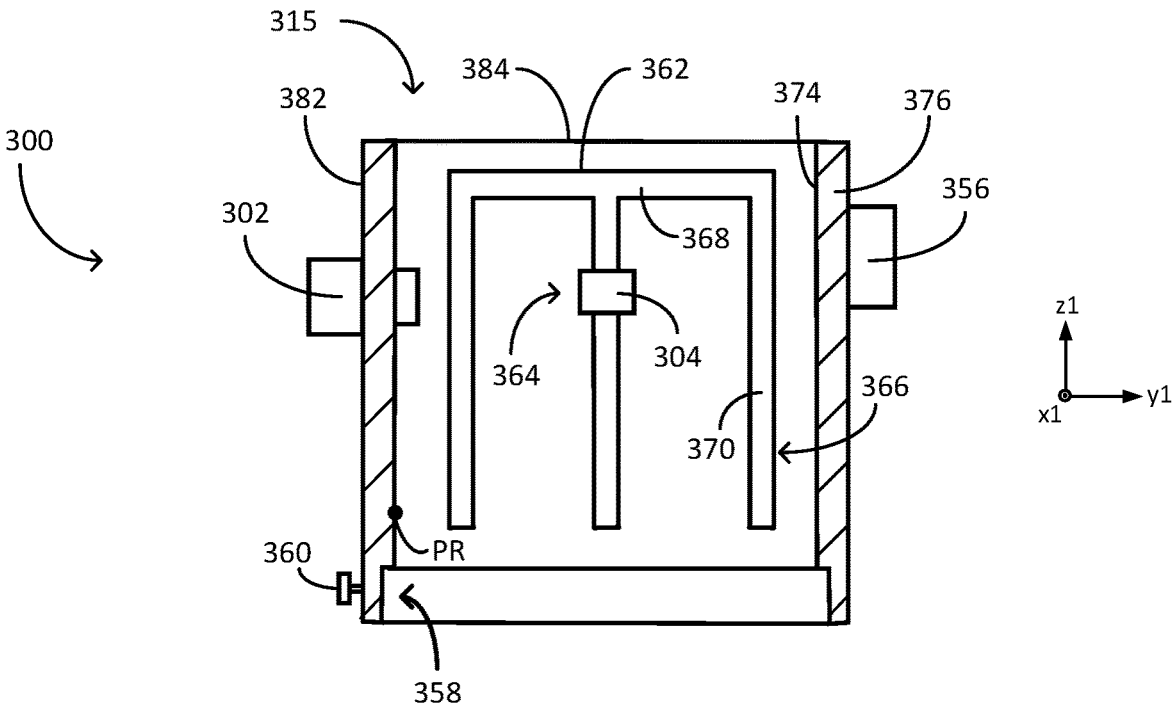
FIG. 7B is a cross-sectional view illustrating the example accuracy system of FIGS. 4-7A.

FIG. 4 illustrates support plate 146 of phantom base 104 mechanically engaged to head frame 119 of stereotactic system 108, such that target point 102 is substantially stationary relative to at least a portion of stereotactic system 108 and the x-y-z coordinate system defined by stereotactic system 108. The translatable components of stereotactic system 108 (e.g., frame member 122, mount 120, carrier platform 128 (FIG. 1)) are positioned such that stereotactic system 108 is in a specific orientation corresponding to the real-space location defined by target point 102. The specific orientation of stereotactic frame 118 causes pointer tip 106 to position in a location displaced from target point 102 by the displacement D. Accuracy system 300 (e.g., processing circuitry 306) may define an x1-y1-z1 coordinate system to define the displacement D. FIG. 5 illustrates a flow diagram depicting example communications among first camera 302, second camera 304, processing circuitry 306, and display 308. FIG. 6 illustrates a representative target location and a representative pointer tip location determined using accuracy system 300. FIG. 7A illustrates a top view of accuracy system 300 projected onto an image plane parallel to plane defined by the x1 axis and the y1 axis of FIG. 4. FIG. 7B illustrates a cross-sectional view of accuracy system 300 projected onto an image plane parallel to plane defined by the y1 axis and the z1 axis of FIG. 2.

First camera 302 defines a first field of view 310 ("first FOV 310") to generate the first image. First FOV 310 may be a solid angle through which an image sensor of first camera 302 is sensitive to light or other electromagnetic radiation. First FOV 310 defines an image plane 311 ("first image plane 311"). The first image may be representative of the location of one or more objects (e.g., pointer tip 106 and/or target point 102) projected onto first image plane 311. Second camera 304 defines a second field of view 312

("second FOV 312") to generate the second image. Second FOV 312 may be a solid angle through which an image sensor of second camera 304 is sensitive to light or other electromagnetic radiation. Second FOV 312 defines an image plane 313 ("second image plane 313"). The second image may be representative of the location of one or more objects (e.g., pointer tip 106 and/or target point 102) projected onto second image plane 313. Accuracy system 300 may be configured to mechanically support first camera 302 and second camera 304 such that first camera 302 and second camera 304 are held substantially stationary relative to each other.

Accuracy system 300 may be configured to mechanically engage phantom base 104 to substantially maintain first camera 302 and second camera 304 substantially stationary relative to some portion of phantom base 104 (e.g., target point 102). In examples, accuracy system 300 mechanically supports first camera 302 and second camera 304 such that first camera 302 (using first FOV 310) and second camera 304 (using second FOV 312) may each capture an image including at least target point 102 when accuracy system 300 mechanically engages phantom base 104. Accuracy system 300 may be configured to mechanically engage phantom base 104 such that such that first camera 302 and second camera 304 may each capture an image including target point 102 and pointer tip 106 when target point 102 and pointer tip 106 are located within volume 114 defined by stereotactic system 108.

In examples, accuracy system 300 includes a gauge frame 315 configured to mechanically engage phantom base 104. Gauge frame 315 may be configured such that at least some portion of gauge frame 315 is substantially stationary relative to phantom base 104 when gauge frame 315 mechanically engages phantom base 104. In examples, gauge frame 315 may be configured to mechanically support first camera 302 and second camera 304 such that first camera 302 and second camera 304 may be substantially stationary relative to phantom base 104 when gauge frame 315 mechanically engages phantom base 104. In examples where accuracy system 300 utilizes a single camera, as discussed above, gauge frame 315 may be configured to mechanically support the single camera in the position of first camera 302 to generate the first image, and configured to mechanically support the single camera in the position of second camera 304 to generate the second image. In examples, accuracy system 300 (e.g., gauge frame 315) is configured to mechanically engage first camera 302 and/or second camera 304 such that first camera 302 and/or second camera 304 is substantially stationary with respect to a fixed point PR on gauge frame 315.

In examples, accuracy system 300 (e.g., gauge frame 315) is configured to mechanically support first camera 302 and second camera 304 such that first FOV 310 and second FOV 312 have differing orientations with respect to the x1-y1-z1 coordinate system defined by accuracy system 300. For example, accuracy system 300 may mechanically support first camera 302 such that an intersection between first image plane 311 of first FOV 310 and a line parallel to the x1 axis defines a first x1 vertex angle, an intersection between first image plane 311 and a line parallel to the y1 axis defines a first y1 vertex angle, and an intersection between first image plane 311 and a line parallel to the z1 axis defines a first z1 vertex angle. The first x1 vertex angle, first y1 vertex angle, and first z1 vertex angle may define the orientation of first FOV 310 with respect to the x1-y1-z1 coordinate system ("first FOV orientation). Accuracy system 300 may mechanically support second camera 304 such that an intersection between second image plane 313 of second FOV 312 and a line parallel to the x1 axis defines a second x1 vertex angle, an intersection between second image plane 313 and a line parallel to the y1 axis defines a second y1 vertex angle, and an intersection between second image plane 313 and a line parallel to the z1 axis defines a second z1 vertex angle. The second x1 vertex angle, second y1 vertex angle, and second z1 vertex angle may define the orientation of second FOV 312 with respect to the x1-y1-z1 coordinate system ("second FOV orientation). In examples, accuracy system 300 mechanically supports first camera 302 and second camera 304 such that the first FOV 310 orientation differs from the second FOV 312 orientation. Stated similarly, accuracy system 300 may mechanically support first camera 302 and second camera 304 such that at least one of the first x1 vertex angle is different than the second x1 vertex angle, the first y1 vertex angle is different from the second y1 vertex angle, or the first z1 vertex angle is different from the second z1 vertex angle.

Accuracy system 300 may be configured to define the first FOV orientation and the second FOV orientation relative to the x1-y1-z1 coordinate system when accuracy system 300 mechanically engages first camera 302 and second camera 304. For example, accuracy system 300 may mechanically engage first camera 302 such that first camera 302 has a defined location with respect to the fixed point PR and/or a defined orientation with respect to the x1-y1-z1 coordinate system. Processing circuitry 306 may be configured to determine the first FOV orientation based on the defined location and/or defined orientation of first camera 302. Accuracy system 300 may mechanically engage second camera 304 such that second camera 304 has a defined location with respect to the fixed point PR and/or a defined orientation with respect to the x1-y1-z1 coordinate system. Processing circuitry 306 may be configured to determine the first FOV orientation based on the defined location and/or defined orientation of first camera 302. Processing circuitry 306 may be configured to determine the second FOV orientation based on the defined location and/or defined orientation of second camera 304.

Hence, accuracy system 300 may be configured to such that the first image generated by first camera 302 (using the first FOV 310 orientation) and the second image generated by second camera 304 (using the second FOV 312 orientation) generate a parallax between the apparent positions of target point 102 and pointer tip 106 in first FOV 310 and the apparent positions of target point 102 and pointer tip 106 in second FOV 312. The parallax generated may be utilized to determine the displacement D between target point 102 and pointer tip 106 using, for example, the position of first camera 302 relative to phantom base 104 (e.g., target point 102, or some other fixed point of phantom base 104), the position of second camera 304 relative to phantom base 104, and the parallax present between the first image and the second image. Processing circuitry 306 may be configured to determine the displacement D using the first image obtained by first camera 302 with the defined first FOV orientation and the second image obtained by second camera 304 with the defined second FOV orientation using, for example, a computer vision technique.

FIGS. 4, 5, 6, 7A, and 7B illustrate accuracy system 300 mechanically supporting first camera 302 and second camera 304 such that first image plane 311 of first FOV 310 is substantially parallel to the x1-z1 plane defined by the x1-y1-z1 coordinate system and second image plane 313 of second FOV 312 is substantially parallel to the y1-z1 plane defied by the x1-y1-z1 coordinate system, however this is not required. Accuracy system 300 may mechanically support first camera 302 and second camera 304 to define other first FOV orientations and second FOV 312 orientations, provided the first FOV 310 orientation and the second FOV orientation result in parallax between the apparent positions of target point 102 and pointer tip 106 in the first image compared to the second image. In some examples, accuracy system 300 may be configured to mechanically support first camera 302 and second camera 304 such that FOV 310 is substantially parallel to one of the x1-z1 plane or the y1-z1 plane and FOV 312 is substantially parallel to the other of the x1-z1 plane or the y1-z1 plane.

Processing circuitry 306 is configured to receive the first image from first camera 302 and receive the second image from second camera 304. Processing circuitry 306 may receive the first image from camera 302 via communication link 314. Processing circuitry 306 may receive the second image from camera 304 via a communication link 316. In examples, where a single camera is utilized for both first camera 302 and second camera 304, processing circuitry may receive the first image and the second image from a single communication link (e.g., one of communication link 314 or communication link 316). The processing circuitry 306 may be configured to substantially recognize (e.g., using imaging recognition software) target 103 and pointer tip 106 in the first image, the second image, and/or in a stereoscopically fused image produced using the first image and the second image. Processing circuitry 306 may be configured to determine an x displacement, a y displacement, and/or a z displacement between target point 102 and pointer tip 106 by substantially comparing the first image and the second image. In examples, processing circuitry 306 is configured to determine a displacement between target point 102 and pointer tip 106 using the parallax generated by first camera 302 and second camera 304 and at least the position of first camera 302 relative to second camera 304 and/or the position second camera 304 relative to first camera 302.

In examples, accuracy system 300 include a probe tip 147 configured to mechanically engage with pointer 110 to assist the first camera 302, second camera 304, and/or processing circuitry 306 in identification of pointer tip 106. Probe tip 147 may include, for example, reflective paint and/or markings configured to assist first camera 302, second camera 304, and/or processing circuitry 306 in identification of pointer tip 106. Probe tip 147 may be configured to mechanically engage pointer 110 to establish a substantially fixed position with respect to pointer tip 106. In some examples, probe tip 147 may mechanically engage pointer 110 such that probe tip 147 substantially defines pointer tip 106 (e.g., probe tip 147 may be configured to insert over and/or cover the end of pointer 110). In some examples, accuracy system 300 includes and/or is configured to utilize a reflective paint or markings on pin 112 of phantom base 104, to assist first camera 302, second camera 304, and/or processing circuitry 306 in identification of pointer tip 106 and/or target point 102.

Processing circuitry 306 may determine the x displacement, the y displacement, and the z displacement as vector components of a position vector extending between target point 102 and pointer tip 106. Processing circuitry 306 may be configured to determine the x displacement as a distance along the x1 axis, the y displacement is a distance along the y1 axis, and the z displacement is a distance along the z1 axis. Processing circuitry 306 may be configured to map the x displacement, the y displacement, and the z displacement to the x-y-z coordinates defined by stereotactic system 108.

In examples, accuracy system 300 is configured such that, when accuracy system 300 (e.g., gauge frame 315) mechanically engages phantom base 104, accuracy system 300 defines the x1-y1-z1 coordinate system in defined orientation relative to a coordinate system xp-yp-zp defined by phantom base 104. Phantom base 104 may be configured such that the xp-yp-zp coordinate system has a defined orientation relative to the x-y-z coordinate system of stereotactic system 108 when phantom base 104 mechanically engages stereotactic system 108. Thus, in examples, processing circuitry 306 may be configured such that when accuracy system 300 mechanically engages phantom base 104 and phantom base 104 is mechanically engaged with stereotactic system 108, processing circuitry may use the defined orientations of the x1-y1-z1 coordinate system and the xp-yp-zp coordinate system to map the x1-y1-z1 coordinate system to the x-y-z coordinate system defined by stereotactic system 108. Processing circuitry 306 may be configured to provide an output to a display 308 indicative of the displacement D mapped to the x-y-z coordinate system of stereotactic system 108. For example, processing circuitry 306 may be configured to provide an output to a display 308 indicative of one or more elements of a vector describing an orientation of the displacement in the x-y-z coordinate system of stereotactic system 108, where each component described a distance determined along the x axis od the x-y-z coordinate system, the y axis of the x-y-z coordinate system, or the z axis of the x-y-z coordinate system.

First camera 302 may be configured to generate a digital image file of the first image captured using first FOV 310. The first image may be representative of objects within FOV 310 projected onto first image plane 311. First camera 302 may represent the first image as a set of picture elements (e.g., pixels) with each picture element describing a numeric representation of a color scale (e.g., a grey level) referenced to a spatial coordinate. As depicted in FIG. 5, first camera 302 may define the spatial coordinate of a picture element within first image plane 311 using an image coordinate system ic1 defined by first camera 302. First camera 302 may be configured to record the set of picture elements describing the first image ("first image picture elements") in a first image file 318.

FIG. 5 pictorially depicts first image file 318 as representative of a first image generated by first camera 302 using first FOV 310 and first image plane 311. First image file 318 includes a set of picture elements describing a first pin image 320 defining a first target location 322. First pin image 320 is an apparent location of a portion of pin 112 when the real-space location of pin 112 within volume V is projected onto first image plane 311. First target location 322 is an apparent location of target point 102 when the real-space location of target point 102 within volume V is projected onto first image plane 311. In similar manner, first image file 318 includes a set of picture elements describing a first pointer image 326 defining a first pointer location 328. First pointer image 326 is an apparent location of a portion of pointer 110 when the real-space location of pointer 110 within volume V is projected onto first image plane 311. First pointer location 328 is an apparent location of pointer tip 106 when the real-space location of pointer tip 106 in volume V is projected onto first image plane 311. First image file 318 may define the spatial coordinates of the picture elements defining first pin image 320, first target location 322, first pointer image 326, and/or first pointer location 328 using the image coordinate system ic1 defined by first camera 302. First camera 302 may be configured to communicate data representative of first image file 318 to processing circuitry 306.

Second camera 304 may be configured to generate a digital image file of the second image captured using second FOV 312. The second image may be representative of objects within FOV 312 projected onto second image plane 313. Second camera 304 may represent the second image as a set of picture elements (e.g., pixels) with each picture element describing a numeric representation of a color scale (e.g., a grey level) referenced to a spatial coordinate. As depicted in FIG. 5, second camera 304 may define the spatial coordinate of a picture element within second image plane 313 using an image coordinate system ic2 defined by second camera 304. Second camera 304 may be configured to record the set of picture elements describing the second image ("second image picture elements") in a second image file 330.

FIG. 5 pictorially depicts second image file 330 as representative of a second image generated by second camera 304 using second FOV 312 and second image plane 313. Second image file 330 includes a set of picture elements describing a second pin image 332 defining a second target location 334. Second pin image 332 is an apparent location of a portion of pin 112 when the real-space location of pin 112 within volume V is projected onto second image plane 313. Second target location 334 is an apparent location of target point 102 when the real-space location of target point 102 within volume V is projected onto second image plane 313. In similar manner, second image file 330 includes a set of picture elements describing a second pointer image 336 defining a second pointer location 338. Second pointer image 336 is an apparent location of a portion of pointer 110 when the real-space location of pointer 110 within volume V is projected onto second image plane 313. Second pointer location 328 is an apparent location of pointer tip 106 when the real-space location of pointer tip 106 in volume V is projected onto second image plane 313. Second image file 330 may define the spatial coordinates of the picture elements defining second pin image 332, second target location 334, second pointer image 336, and/or second pointer location 338 using the image coordinate system ic2 defined by second camera 304. Second camera 304 may be configured to communicate data representative of second image file 330 to processing circuitry 306.

First camera 302, first image file 318, second camera 304, and/or second image file 330 may represent the first image and/or second image as a raster image, a vector image, a combination of the two, or in some other manner. In examples, first camera 302 and/or second camera 304 defines one or more fiducial markers such as fiducial markers 340, 341 defined by first camera 302 within image coordinate system ic1 and fiducial markers 342, 343 defined by second camera 304 within image coordinate system ic2. First camera 302 and/or second camera 304 may define the spatial coordinate of a picture element with reference to fiducial markers 340, 341, 342, 343. Although represented as imaged elements within first image file 318 and second image file 330 for clarity, first camera 302 and/or second camera 304 may be configured to define the location of fiducial markers 340, 341, 342, 343 within first image file 318 and/or second image file 330 without representing fiducial markers 340, 341, 342, 343 as imaged objects.

Processing circuitry 306 is configured to determine the displacement D using first image file 318 and second image file 330. As discussed, processing circuitry may be configured to determine the first FOV orientation of first camera 302 utilized to generate first image file 318 and the second FOV orientation of second camera 304 utilized to generate second image file 330. Processing circuitry 306 may be configured to perform a computer vision technique using the first FOV orientation, first image file 318, the second FOV orientation, and second image file 330 to determine the displacement D. Processing circuitry may be configured to determine the displacement D using the computer vision technique and map the displacement D to the coordinates of the x-y-z coordinate system of stereotactic system 108 (e.g., when accuracy system 300 mechanically engages phantom base 104 and phantom base 104 mechanically engages stereotactic system 108). Processing circuitry 306 may provide an output to display 308 indicative of the displacement D using, for example, communication link 339.

In examples, processing circuitry 306 is configured to utilize a computer vision technique based on first target location 322, first pointer location 328, second target location 334, and/or second pointer location 338 to determine the displacement D. Processing circuitry 306 may be configured to define first target location 322, first pointer location 328, second target location 334, and/or second pointer location 338 to determine the displacement D. For example, processing circuitry 306 may be configured to process the first image picture elements of first image file 318 to conduct object recognition (e.g., using image recognition software and/or other computer vision software) to define first target location 322 and first pointer location 328. Processing circuitry 306 may be configured to conduct image classification and/or object localization using the first image picture elements to substantially recognize first target location 322 and first point location 328 within the first image. Processing circuitry 306 may be configured to process the second image picture elements of second image file 330 to conduct object recognition to define second target location 334 and second pointer location 338. Processing circuitry 306 may be configured to conduct image classification and/or object localization using the second image picture elements to substantially recognize second target location 334 and second pointer location 338 within the second image.

Processing circuitry 306 may be configured to define and/or recognize first target location 322, first pointer location 328, second target location 334, and/or second pointer location 338 using a variety of techniques. In examples, processing circuitry 306 is configured to define and/or recognize first target location 322, first pointer location 328, second target location 334, and/or second pointer location 338 using a training data base describing photometric and/or geometric properties of one or more of pin 112, target point 102, pointer 110, and/or pointer tip 106. Processing circuitry 306 may define or retrieve one or more templates describing one or more of pin 112, target point 102, pointer 110, and/or pointer tip 106 and substantially scan the first image picture elements and the second picture elements using a template at different locations, scales, rotations, and other orientations to determine first target location 322, first pointer location 328, second target location 334, and/or second pointer location 338.

In examples, the computer vision technique of processing circuitry 306 is configured to conduct triangulation (e.g., reconstruction, intersection) to determine points in a three-dimensional space using corresponding points in first image file 318 and second image file 330. A corresponding point may include a first point (or set of points) within image file 318 and a second point (or set of points) within second image file 330, where the first point and the second point image a key point of an object defined within both the first image of first camera 302 and the second image of second camera 304 (e.g., target point 102 or pointer tip 106). Processing circuitry 306 may be configured to define an first epipolar line using the first point and the first FOV orientation and a second epipolar line using the second point and the second FOV orientation, and a determine a location of the key point of the object in a three-dimensional space defined by the x1-y1-z1 coordinate system using the first epipolar line and the second epipolar line. In examples, the first epipolar line is a first line passing through first FOV 310 from first camera 302 and substantially intersecting the first point in first image plane 311. The second epipolar line may be a second line passing through second FOV 312 from second camera 304 and substantially intersecting the second point in second image plane 313. The computer vision technique of processing circuitry 306 may be configured to determine a location of the key point based on an intersection of the first epipolar line and the second epipolar line with a point or neighborhood of points in the x1-y1-z1 coordinate system. Thus, the computer vision technique pf processing circuitry 306 may be configured to determine a location of the key point in the x1-y1-z1 system when the key point is images within the first image of first camera 302 and the second image of second camera 304.

Processing circuitry 306 may be configured to use a first set of corresponding points describing first target location 322 and second target location 334 to determine a representative location of target point 102 in the x1-y1-z1 coordinate system. In examples, processing circuitry 306 is configured to triangulate the first set of corresponding points to determine the representative location of target point 102 in the x1-y1-z1 coordinate system. As an example, FIG. 6 illustrates accuracy system 300 defining a representative location 344 of target point 102 "representative target point location 344") using first target location 322 of first image file 318 and second target location 334 of second image file 330 as the first set of corresponding points. Processing circuitry 306 defines a first epipolar line 346 passing from first camera 302 through first target location 328 and a second epipolar line 348 passing from second camera 304 through second target location 334. Processing circuitry 306 uses first epipolar line 346 and second epipolar line 348 to define representative target point location 344 within the x1-y1-z1 coordinate system of accuracy system 300.

In similar manner, processing circuitry 306 may be configured to use a second set of corresponding points describing first pointer location 328 and second pointer location 338 to determine a representative location 350 of pointer tip 106 ("representative pointer tip location 350") in the x1-y1-z1 coordinate system. Processing circuitry 306 may be configured to triangulate the second set of corresponding points to determine representative pointer tip location 350. As an example, FIG. 6 illustrates accuracy system 300 defining representative pointer tip location 350 using first pointer location 328 of first image file 318 and second pointer location 338 of second image file 330 as the second set of corresponding points. Processing circuitry 306 defines a third epipolar line 352 passing from first camera 302 through first pointer location 328 and a fourth epipolar line 354 passing from second camera 304 through second pointer location 338. Processing circuitry 306 uses third epipolar line 352 and fourth epipolar line 354 to define representative pointer tip location 350 within the x1-y1-z1 coordinate system of accuracy system 300.

Processing circuitry 306 may be configured to determine a displacement between representative target point location 344 and representative pointer tip location 350 in order to determine the displacement D between target point 102 and pointer tip 106. Processing circuitry 306 may determine the displacement between representative target point location 344 and representative pointer tip location 350 in a form indicative of a displacement $\Delta z$ parallel to the z1 axis, a displacement $\Delta x$ parallel to the x1 axis, and/or a displacement $\Delta y$ parallel to the y1 axis. Processing circuitry 306 may be configured to map the displacement between representative target point location 344 and representative pointer tip location 350 from the x1-y1-z1 coordinate system to the xp-yp-zp coordinate system of phantom base 104 and/or the x-y-z coordinate system of stereotactic system 108. Processing circuitry 306 may provide an output to display 308 indicative of the displacement D.

FIG. 7A illustrates a top view of accuracy system 300 projected onto an image plane parallel to plane defined by the x1 axis and the y1 axis of FIG. 4. Gauge frame 315 mechanically supports first camera 302 and second camera 304 such that first camera 302 and second camera 304 define first FOV 310 (FIGS. 4, 5) and second FOV 312 having differing orientations with respect to the x1-y1-z1 coordinate system of accuracy system 300. In examples, gauge frame 315 includes a housing 356 configured to mechanically support processing circuitry 306 and/or display 308 (FIGS. 4-6), although this is not required. In some examples, processing circuitry 306 and/or display 308 may be mechanically supported by housing substantially separate from gauge frame 315, such as a laptop, tablet, other personal computing device, or other computer apparatus. FIG. 7B illustrates a cross-sectional view of accuracy 300 projected onto an image plane parallel to plane defined by the y1 axis and the z1 axis of FIG. 7A and taken with reference to cutting plane A-A' of FIG. 7A.

Gauge frame 315 may include an engagement structure 358 configured to mechanically engage phantom base 104 and/or stereotactic system 108 to, for example, maintain first camera 302 and second camera 304 substantially stationary relative to phantom base 104 and/or stereotactic system 108. In examples, gauge frame 315 includes an engagement structure 358 configured to mechanically engage phantom base 104 and/or stereotactic system 108. Engagement structure 358 may be configured to mechanically engage phantom base 104 and/or stereotactic system 108 in any manner sufficient to maintain first camera 302 and second camera 304 substantially stationary relative to phantom base 104 and/or stereotactic system 108 when engagement structure 358 mechanically engages phantom base 104 and/or stereotactic system 108.

In examples, engagement structure 358 is configured to mechanically engage some portion of phantom base 104 (FIG. 1). Engagement structure 358 may be configured to mechanically engage some portion of a perimeter defined by phantom base 104 (FIG. 1). In examples, engagement structure 358 may be configured to engage a portion of a closed perimeter defined within the xp-yp plane of phantom base 104. In some examples, engagement structure 358 is configured to mechanically engage at least some portion of a perimeter defined by support plate 146.

Engagement structure 358 may mechanically engage phantom base 104 in any manner to cause accuracy system 300 to mechanically engage phantom base. In examples, engagement structure 358 is configured to slidably translate over a portion of phantom base 104 (e.g., a portion of support plate 146) when engagement structure 358 mechanically engages phantom base 104. Engagement structure 358 may be configured such that, when engagement structure is slidably translated over phantom base in a first direction (e.g., in a direction parallel to the zp direction (FIG. 4)), engagement structure 358 substantially resists motion of gauge frame 315 relative to phantom base 104 in a second direction and/or a third direction orthogonal to the first direction (e.g., in a direction parallel to the xp direction and/or yp direction (FIG. 4)). In some examples, gauge frame 315 (e.g., engagement structure 358) is configured to mechanically engage at least a first portion of phantom base 104 and a second portion of phantom base 104, such that the mechanical engagement of the first portion substantially resists motion of gauge frame 315 in the first direction and the mechanical engagement of the second portion substantially resists motion of gauge frame 315 in a second direction substantially opposite the first direction. In some examples, a portion of gauge frame 315 is configured to substantially surround support plate 146 when engagement structure 358 mechanically engages phantom base 104.

Engagement structure 358 may be configured in any manner to resist motion of gauge frame 315 relative to phantom base 104. Engagement structure 358 may be configured to frictionally engage phantom base 104 to maintain gauge frame 315 substantially stationary with respect to phantom base 104. Engagement structure 358 may be configured to frictionally engagement phantom base 104 in any manner sufficient to cause engagement structure 358 to resist motion of gauge frame 315 relative to phantom base in at least one direction (e.g., a direction parallel to the xp axis, yp axis, and/or zp axis). In examples, gauge frame 315 may be configured such that engagement structure 358 substantially compresses against phantom base 104 (e.g., compresses against a portion of support plate 146) when engagement structure 358 mechanically engages phantom base 104. For example, gauge frame 315 may be configured such that the mechanical engagement of engagement structure 358 and phantom base 104 causes a deformation of a portion of gauge frame 315 when engagement structure 358 mechanically engages phantom base 104. Gauge frame 315 may be resiliently biased such that the deformation causes engagement structure 358 to substantially compress against phantom base 104 (e.g., as the resilient biasing attempts to return gauge frame 315 to a substantially zero-stress position). In examples, engagement structure 358 may be configured to form a snap-fit, an interference fit, or some other fit with phantom base 104 when gauge frame 315 mechanically engages phantom base 104. In some examples, one of engagement structure 358 or phantom base 104 (e.g., support plate 146) defines a protrusion and the other of engagement structure 358 or phantom base 104 (e.g., support plate 146) defines a recess configured to receive the protrusion when gauge frame 315 mechanically engages phantom base 104.

In examples, engagement structure 358 includes a clamping component 360 configured to cause gauge frame 315 to exert a clamping force on phantom base 104 when clamping component 360 is moved (e.g., by a practitioner) relative to gauge frame 315. Clamping component 360 may be, for example, a lever, a thumbscrew, or some other mechanism configured to cause gauge frame 315 to exert the clamping force. In some examples, clamping component 360 comprises a first section and a second section separable from the first section. The first section and the second section may be configured to mechanically mate to form a substantially unified portion of clamping component 360. Clamping component 360 may be configured such that mechanically mating the first portion and the second portion causes gauge frame 315 to exert the clamping force on phantom base 104. The first component and the second component may comprise, for example, a stud and a socket (e.g., a snap fastener), a latch and a catch, a barrel bolt and a catch plate, or any other components configured to form a mechanically mated connection with each other. Clamping component 360 may be configured to decrease the clamping force exerted by gauge frame 315 on phantom base 104 when clamping component 360 is moved (e.g., by a practitioner) relative to gauge frame 315 to, for example, allow the removal of gauge frame 315 from phantom base 104 or the further translation of gauge frame 315 with respect to phantom base 104.

Gauge frame 315 may be configured to mechanically support first camera 302 and/or second camera 304 in a plurality of different positions, such that first camera 302 and/or second camera 304 may alter the orientation of defined field of view. For example, gauge frame 315 may be configured to mechanically support second camera 304 generally in a first location 364 as indicated in FIG. 7B, such that second FOV 312 establishes a first orientation with respect to the x1-y1-z1 axis of accuracy system 300. In addition to the first location 364, gauge frame 315 may be configured to mechanically support second camera 304 generally in a second location 366 indicated in FIG. 7B, such that second FOV 312 establishes a second orientation with respect to the x1-y1-z1 axis of accuracy system 300. Hence, gauge frame 315 may be configured such that second camera 304 may capture one second image from first location 364 and another second image from second location 366. Gauge frame 315 may be configured to mechanically support second camera 304 at the different locations to, for example, cause second FOV 312 to shift as different pins of phantom base 104 (e.g., pin 142) are utilized to determine a displacement between pointer tip 106 and a target point defined by of phantom base 104. In examples, gauge frame 315 is configured to mechanically support first camera 302 and/or second camera 304 in a plurality of positions relative to the fixed point PR such that first FOV 310 and/or second FOV 312 may be substantially aligned with an individual target point by an individual pin of phantom base 104 when gauge frame 315 mechanically engages phantom base 104.

In examples, gauge frame 315 includes a track 362 configured to mechanically support a camera (e.g., second camera 304). Track 362 may be configured such that second camera 304 may be translated (e.g., by a practitioner) as track 362 mechanically supports camera 304. For example, track 362 may be configured to mechanically support second camera 304 generally at first location 364 or generally at second location 366. Track 362 may be configured such that second camera 304 may be translated (e.g., by a practitioner) on track 362 to position at first location 364, second location 366, or another location defined by track 362. In examples, second camera 304 is configured to slidably translate on track 362 to position at first location 364, second location 366, or another location defined by track 362. Track 362 may be configured to allow camera 304 to translate in any orientation with respect to the x1-y1-z1 coordinate system of accuracy system 300. Track 362 may be configured to allow camera 304 to translate in any orientation with respect to the xp-yp-zp coordinate system of phantom base 104 when gauge frame 315 mechanically engages phantom base 104. In examples, track 362 is configured such that second camera 304 may translate on track 362 in a direction substantially parallel to one or more of the xp axis, the yp axis, and/or the zp axis of the xp-y-zp coordinate system of phantom base 104 when gauge frame 315 mechanically engages phantom base 104. For example, as illustrated in FIG. 7B, track 362 may include a first section 368 configured to allow second camera 304 to translate in a direction substantially parallel to the yp axis of phantom base 104 when gauge frame 315 mechanically engages phantom base 104, and may include a second section 370 configured to allow second camera 304 to translate in a direction substantially parallel to the zp axis of phantom base 104 when gauge frame 315 mechanically engages phantom base 104.

Gauge frame 315 may define a backdrop surface 374 configured to provide background to a first image or a second image capturing target point 102 (FIGS. 4, 5) and pointer tip 106. Backdrop surface 374 may be configured to provide a degree of contrast between target point 102 and pointer tip 106 in the first image defined by first image file 418 and/or the second image defined by second image file 330. Backdrop surface 374 may be configured to facilitate the discrimination of processing circuitry 306 when processing circuitry 306 defines first target location 322, first pointer location 328, second target location 334, second pointer location 338, and or other portions of pin 112 or pointer 110. Backdrop surface 374 may define a solid-colored surface, a black- and white or colored patterned surface, a three-dimensionally textured surface, and/or a surface having other one or more other surface attributes configured to provide contrast between target point 102 and pointer tip 106 in a first image and/or a second image.

In examples, gauge frame 315 includes a wall 376 including backdrop surface 374. Gauge frame 315 may mechanically support wall 376 such that backdrop surface 374 positions within a field-of view defined by a camera of accuracy system 300 (e.g., within FOV 310 of first camera 302). In examples, gauge frame 315 mechanically supports wall 376 such that, when gauge frame 315 mechanically engages phantom base 104, one or more pins (e.g., pin 112) defined by phantom base 104 is between first camera 302 and backdrop surface 374. In examples, gauge frame 315 includes wall 376 configured to position backdrop surface 374 in FOV 310 of first camera 302 when gauge frame supports first camera 302. Gauge frame 315 may include a wall 378 configured to position a backdrop surface 380 in FOV 312 of second camera 304 when gauge frame supports second camera 304.

In some examples, gauge frame 315 includes a wall 382 configured to mechanically support first camera 302. Gauge frame 315 may include a wall 384 configured to mechanically support second camera 304. In examples, wall 382 and/or wall 384 defines a track (e.g., track 362) configured to support first camera 302 and/or second camera 304 in a plurality of positions relative to fixed point PR on gauge frame 315. Any of or some combination of wall 376, wall 378, wall 382, and/or wall 384 may define engagement structure 358. In examples, two or more of wall 376, wall 378, wall 382, and/or wall 384 define a corner configured to conform with a perimeter defined by support plate 146 when gauge frame 315 mechanically engages phantom base 104. In some examples, each of wall 376, wall 378, wall 382, and wall 384 is secured to at least two other of wall 376, wall 378, wall 382, or wall 384, such that wall 376, wall 378, wall 382, and wall 384 define a closed perimeter. Gauge frame 315 may mechanically support wall 376, wall 378, wall 382, and wall 384 such that the closed perimeter conforms with a perimeter defined by support plate 146 when gauge frame 315 mechanically engages phantom base 104.

Processing circuitry 306 may include one or more processors that are configured to implement functionality and/or process instructions for execution within accuracy system 300. Processing circuitry 306 may include, for example, microprocessors, DSPs, ASICs, FPGAs, or equivalent discrete or integrated logic circuitry, or a combination of any of the foregoing devices or circuitry. Processing circuitry 174 may be capable of processing instructions stored in a storage device. The storage device may include a computer-readable storage medium or computer-readable storage device. In some examples, the storage device includes one or more of a short-term memory or a long-term memory, such as RAM, DRAM, SRAM, magnetic discs, optical discs, flash memories, or forms of EPROM or EEPROM. The storage device may be, for example, any fixed or mobile computer system (e.g., a controller, a microcontroller, a personal computer, minicomputer, tablet computer, etc.). In examples, the storage device is configured to store data indicative of instructions for execution by processing circuitry 306. The storage device may be used by software or applications running on processing circuitry 306 to temporarily store information during program execution. Accordingly, processing circuitry 306 may include any suitable structure, whether in hardware, software, firmware, or any combination thereof, to perform the functions ascribed herein to processing circuitry 306.

Communication links 136, 140, 314, 316, 339 may include any suitable hardware, firmware, software or any combination thereof for communicating with another device, such as drive motor 130, circuitry 134, input device 138, processing circuitry 306, display 308, first camera 302, second camera 304, and/or others. Communication links 136, 140, 314, 316, 339 may be configured to receive and/or send communications under the control of circuitry 134 and/or processing circuitry 306. Circuitry 134 and/or processing circuitry 306 may be configured to send and receive communications via communication links 136, 140, 314, 316, 339. In examples, circuitry 134 and/or processing circuitry 306 are configured to send communications to and/or receive communications, including downlink and uplink telemetry, from components not shown in FIGS. 1-7B. Circuitry 134 and/or processing circuitry 306 may be configured to transmit or receive signals via inductive coupling, electromagnetic coupling, Near Field Communication (NFC), Radio Frequency (RF) communication, Bluetooth, Wi-Fi, or other proprietary or non-proprietary wireless communication schemes, including wired and/or wireless communication and/or network protocols.

Display 308 may include a visual display, with which processing circuitry 306 may present information related to a displacement D between target point 102 and pointer tip 106. In addition, display 308 may include an input mechanism to receive input from a practitioner. The input mechanisms may include, for example, any one or more of buttons, a keypad (e.g., an alphanumeric keypad), a peripheral pointing device, a touch screen, or another input mechanism that allows the practitioner to navigate through user interfaces presented by processing circuitry 306 and provide input. Display 308 may include audio circuitry for providing audible notifications, instructions or other sounds to the practitioner, receiving voice commands from the practitioner, or both.

Figure 8:
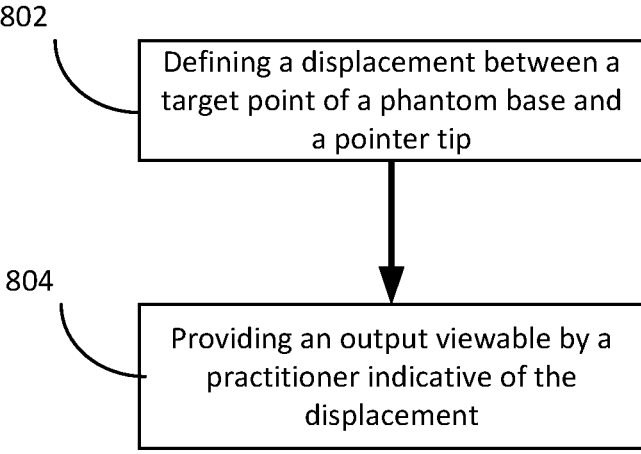
FIG. 8 illustrates an example technique for determining a displacement D between a target point of a phantom base and a pointer tip of a stereotactic system.

A technique for determining an accuracy of a stereotactic system is illustrated in FIG. 8. Although the technique is described mainly with reference to accuracy system 100, 200, 300 of FIGS. 1-7B, the technique may be applied to other accuracy systems in other examples.

The method includes defining, using accuracy system 100, 200, 300, a displacement D between a target point 102, 144 defined by phantom base 104 and a pointer tip 106 of a stereotactic system 108 (802). Accuracy system 100, 200, 300 may mechanically engage phantom base 104 when accuracy system 100, 200, 300, defines the displacement D.

In examples, phantom base 104 mechanically engages stereotactic frame 118 when accuracy system 100, 200, 300 mechanically engages phantom base 104. In examples, stereotactic frame defines a volume V, and phantom base 104 define target points 102, 144 within the volume V when phantom base 104 mechanically engages stereotactic frame 118. The technique may include positioning pointer tip 106 within volume V in the vicinity of target points 102, 144.

Accuracy system 100, 200, 300 may define a spatial relationship between pointer tip 106 and target point 102, 144 and provide an output indicative of the spatial relationship when accuracy system 100, 200, 300 mechanically engages phantom base 104 (804). Accuracy system 100, 200, 300 may provide a displacement D indicative the spatial relationship. In examples, accuracy system 100, 200 provides the output using one or more x-y visible indicia 213 and/or one or more z visible indica 217. In examples, accuracy system 100, 300 provide the output to a display 308.

In examples, a gauge support 202 of accuracy system 100, 200 mechanically engages phantom base 104 when accuracy system 100, 200 defines the displacement D. Gauge support 202 may mechanically engage pin 112, 142. At last some portion of accuracy system 100, 200 may remain substantially stable relative to phantom base 104 when gauge support 202 mechanically engages phantom base 104. Accuracy system 100, 200 may defines an origin O1 of an x1-y1-z1 coordinate system when gauge support 202 mechanically engages phantom base 104. In examples, accuracy system 100, 200 defines an origin O1 of its x1-y1-z1 coordinate system substantially at target point 102, 144 when gauge support 202 mechanically engages phantom base 104.

Gauge support 202 may mechanically engage a pin body 115 of pin 112 when gauge support 202 mechanically engages phantom base 104. Gauge support 202 may substantially surround at least a portion of pin body 115 and a pin axis P extending through pin body 115 when gauge support 202 mechanically engage pin body 115. Gauge support 202 may substantially surround pin body 115 over a portion of or substantially the entirety of a displacement DP defined by pin body 115. Gauge base 204 may at least partially define the displacement D between target point 102, 144 and pointer tip 106 when gauge support 202 mechanically engages pin 112, 142. In examples, a gauge base surface 206 configured to define the x1 axis and the y1 axis of the x1-y1-z1 coordinate system. Gauge base surface 206 defines an x1 axis and a y1 axis of the x1-y1-z1 coordinate system when gauge support 202 mechanically engages phantom base 104. Gauge base surface 206 may defines the x1 axis and the y1 axis substantially perpendicularly to the pin axis P when gauge support 202 mechanically engages phantom base 104.

A z-member surface 210 of a z-member 208 may define a z displacement between target point 102, 144 and pointer tip 106 when gauge support 202 mechanically engages phantom base 104. Z-member surface 210 may define the z1 axis substantially perpendicular to at least one of the x1 axis and the y1 axis gauge base surface 206. In examples, accuracy system 100, 200 establishes the z1 axis in a defined orientation relative to the pin axis P and establishes the x1-y1 plane in a defined orientation relative to pin axis P when gauge support 202 mechanically engages pin 112, 142.

Accuracy system 100, 200 may align pin 112, 142 such the x1 axis, the y1 axis, and the z1 axis each define a distance along the respective axes from a portion of pin 112, 142 (e.g., target point 102, 144) when gauge support 202 mechanically engages pin 112, 142. Accuracy system 100, 200 may demarcate distance along the x1 axis and the y1 axis using one or more x-y visible indicia 213 when gauge support 202 mechanically engages pin 112, 142. Accuracy system 100, 200 may demarcate distance along the z1 axis using one or more z visible indicia 218 when gauge support 202 mechanically engages pin 112, 142. Accuracy system 100, 200 may output indicating the x displacement, the y displacement, and/or the z displacement to a practitioner using x-y visible indicia 213 and/or the z visible indicia 217.

Gauge support 202 may substantially grip a portion of pin body 115 when gauge support 202 mechanically engages pin 112. One or more grip elements such as grip element 234 and grip element 236 may engage pin body 115 to substantially grip pin body 115 when gauge support 202 mechanically engages pin 112. Grip element 234, 236 may frictionally engage pin body 115 such that exertion of a force by a practitioner causes translation of gauge support 202 relative to pin body 115. Clamping mechanism 238 may cause grip element 234, 236 to exert an inward clamping force on pin body 115 when clamping mechanism 238 moves (e.g., is moved by a practitioner) relative to gauge support 202. In examples, clamping mechanism 238 decreases the inward clamping force exerted by grip element 234, 236 on pin body 115 when clamping mechanism 238 is moved (e.g., by a practitioner) relative to gauge support 202.

In examples, accuracy system 100, 300 determines the displacement D using two or more images of target point 102 and pointer tip 106. Accuracy system 100, 300 may capture a first image of target point 102 and pointer tip 106 and a second image of target point 102 and pointer tip 106 and determine the displacement D using the first image and the second image. Accuracy system 100, 300 may mechanically support a first camera 302 and a second camera 304 such that the first image and the second image generate a parallax between the apparent positions of target point 102 and pointer tip 106. Processing circuitry 306 may determine the displacement D by comparing the first image and the second image. Processing circuitry 306 may provide an output to a display 308 indicating the displacement D.

First camera 302 may generate the first image using a first FOV 310 defining a first image plane 311. Second camera 304 may generate the second image using a second FOV 312 defining a second image plane 313. Accuracy system 100, 300 may establish first FOV 310 in an orientation relative to the x1-y1-z1 coordinate system different from an orientation of second FOV 312 relative to the x1-y1-z1 system when accuracy system 100, 300 mechanically engages phantom base 104. Accuracy system 100, 300 may mechanically support first camera 302 and second camera 304 such that first camera 302 and second camera 304 are held substantially stationary relative to each other.

The technique may include mechanically supporting first camera 302 and second camera 304 using gauge frame 315. The technique may include capturing a first image using first camera 302 and first FOV 310 and capturing a second image using camera 304 and second FOV 312. Gauge frame 315 may mechanically engage phantom base 104. Accuracy system 100, 300 may define the first FOV orientation of first FOV 310 and the second FOV orientation of FOV 312 relative to the x1-y1-z1 coordinate system when accuracy system 100, 300 mechanically engages phantom base 104. In examples, processing circuitry 306 determines the first FOV orientation based on the defined location and/or defined orientation of first camera 302 and/or determines the second FOV orientation based on the defined location and/or defined orientation of second camera 304.

Processing circuitry may receive a first image file 318 representative of the first image from first camera 302 and receive a second image file 330 representative of the second image from second camera 304. Processing circuitry 306 may determine the displacement D using first image file 318 and second image file 330. In examples, processing circuitry 306 performs a computer vision technique using the first FOV orientation, first image file 318, the second FOV orientation, and second image file 330 to determine the displacement D. Processing circuitry 306 may determine the displacement D using the computer vision technique and map the displacement D to the coordinates of the x-y-z coordinate system of stereotactic system 108 (e.g., when accuracy system 300 mechanically engages phantom base 104 and phantom base 104 mechanically engages stereotactic system 108).

In examples, processing circuitry 306 conducts the computer vision technique based on first target location 322, first pointer location 328, second target location 334, and/or second pointer location 338. Processing circuitry 306 may define first target location 322, first pointer location 328, second target location 334, and/or second pointer location 338 to determine the displacement D. In examples, processing circuitry 306 defines first target location 322 and first pointer location 328 by processing first image file 318 to conduct object recognition. Processing circuitry 306 may define second target location 334 and second pointer location 338 by processing second image file 330 to conduct object recognition.

Processing circuitry 306 may define one or more epipolar lines using first target location 322, first pointer location 328, second target location 334, and/or second pointer location 338, Processing circuitry 306 may triangulate a representative target point location 344 of target point 102, 144 and a representative target pointer tip location 350 of pointer tip 106 using the one or more epipolar lines. Processing circuitry 306 may determine a displacement between representative target point location 344 and representative pointer tip location 350 in order to determine the displacement D. Processing circuitry 306 may map the displacement between representative target point location 344 and representative pointer tip location 350 from the x1-y1-z1 coordinate system to the xp-yp-zp coordinate system of phantom base 104 and/or the x-y-z coordinate system of stereotactic system 108 and provide an output to display 308 indicative of the displacement D.

Gauge frame 315 may mechanically support first camera 302 and/or second camera 304 using a track 362. First camera 302 and/or second camera 304 may translate over track 362 as track 362 mechanically supports first camera 302 and/or second camera 304. In examples, track 362 allows translation of second camera 304 from at first location 364 to a second location 366 of track 362. In examples, second camera 304 translates on track 362 in a direction substantially parallel to one or more of the xp axis, the yp axis, and/or the zp axis of the xp-y-zp coordinate system of phantom base 104 when gauge frame 315 mechanically engages phantom base 104. In examples, second camera 304 translates on track 362 in a direction substantially parallel to one or more of the x axis, the y axis, and/or the z axis of the x-y-z coordinate system of stereotactic system 108 when gauge frame 315 mechanically engages phantom base 104 and phantom base 104 mechanically engages stereotactic system 108.

Gauge frame 315 position a backdrop surface 374 to provide background to a first image or a second image capturing target point 102 and pointer tip 106 when gauge frame 315 mechanically engages phantom base 104. In examples, gauge frame 315 mechanically supports a wall 376 configured to position backdrop surface 374 within first FOV 310 of first camera 302 when gauge frame mechanically engages phantom base 104. Gauge frame 315 may mechanically supports wall 376 such that pins 112, 142 are between first camera 302 and backdrop surface 374 when gauge frame 315 mechanically engages phantom base 104. In examples, gauge frame 315 positions a backdrop surface 380 of wall 378 in second FOV 312 of second camera 304 when gauge frame supports second camera 304.

Gauge frame 315 may mechanically support first camera 302 using a wall 382. In examples, gauge frame 315 mechanically supports second camera 304 using wall 384. Wall 382 and/or wall 384 may define a track (e.g., track 362) configured to support first camera 302 and/or second camera 304 in a plurality of positions relative to fixed point PR on gauge frame 315. In examples, one or more of wall 376, wall 378, wall 382, and/or wall 384 defines engagement structure 358. Two or more of wall 376, wall 378, wall 382, and/or wall 384 may define a corner conforming with a perimeter defined by support plate 146 when gauge frame 315 mechanically engages phantom base 104. In examples, gauge frame 315 mechanically supports wall 376, wall 378, wall 382, and wall 384 such that a closed perimeter defined by wall 376, wall 378, wall 382, and wall 384 conforms with the perimeter defined by support plate 146 when gauge frame 315 mechanically engages phantom base 104.

The disclosure includes the following examples.

Example 1: A system configured to determine an accuracy of a stereotactic frame, wherein the system is configured to: define an x displacement from a target point of a phantom base mechanically engaging the stereotactic frame to a pointer tip of the stereotactic frame when the pointer tip is placed at a pointer tip location, wherein the x displacement is a distance parallel to an x axis in an x-y-z coordinate system; define a y displacement from the target point to the pointer tip when the pointer tip is placed in the pointer tip location, wherein the y displacement is a distance parallel to a y axis in the x-y-z coordinate system; define a z displacement from the target point to the pointer tip when the pointer tip is placed in the pointer tip location, wherein the z displacement is a distance parallel to a z axis in the x-y-z coordinate system; and provide an output viewable by a practitioner, wherein the output indicates one or more of the x displacement, the y displacement, or the z displacement.

Example 2: The system of example 1, wherein a portion of the system is configured to remain substantially stationary relative to a point in the x-y-z coordinate system.

Example 3: The system of example 1 or example 2, wherein the system is configured to define an origin of the x-y-z coordinate system substantially at the target point of the phantom base.

Example 4: The system of any of examples 1-3, wherein a portion of the system is configured to remain substantially stationary relative to the target point.

Example 5: The system of example 4, wherein the portion of the system is a first portion, and wherein a second portion of the system is configured to move relative to the target point when the first portion remains substantially stationary relative to the target point.

Example 6: The system of any of examples 1-5, wherein the pointer the pointer tip location is a first pointer tip location, and wherein the system is configured to: define a second x displacement when the pointer tip is placed in a second pointer tip location, a second y displacement when the pointer tip is placed in the second pointer tip location, and a second z displacement when the pointer tip is placed in the second pointer tip location; and provide a second output viewable by a practitioner, wherein the second output indicates one or more of the second x displacement, the second y displacement, and the second z displacement.

Example 7: The system of any of examples 1-6, wherein the system is configured to determine the x displacement, the y displacement, and the z displacement for each of a plurality of target points defined by the phantom base.

Example 8: The system of any of examples 1-7, wherein the system defines the x-y-z coordinate system.

Example 9: The system of example 8, wherein the system is configured to map the x-y-z coordinate system to a coordinate system defined by the phantom base.

Example 10: The system of any of examples 1-9, wherein the x-y-z coordinate system defines one or more locations in an intercranial space of a patient, and wherein the system is configured to: define at least one of the x displacement or a the y displacement on a horizontal anatomical plane defined by the intercranial space; and define the z displacement on at least one of a medial anatomical plane defined by the intercranial space or a coronal anatomical plane defined by the intercranial space of the patient.

Example 11: The system of any of examples 1-10, wherein the x-y-z coordinate system defines one or more locations in an intercranial space of a patient, and wherein the system is configured to: define one of the x displacement or the y displacement substantially parallel to an anterior or posterior direction of the patient and define the other of the x displacement or the y displacement substantially parallel to a left lateral or a right lateral direction of the patient; and define the z displacement substantially parallel to a superior or inferior direction of the patient.

Example 12: The system of any of examples 1-11, further comprising a gauge support configured to mechanically engage a pin of the phantom base, wherein the pin defines the target point.

Example 13: The system of example 12, wherein the x-y-z coordinate system is a primary coordinate system defined by the phantom base, wherein the gauge support defines a secondary x-y-z coordinate system, and wherein the gauge support is configured to substantially align the secondary coordinate system with the primary coordinate system when the gauge support mechanically engages the pin.

Example 14: The system of example 12 or example 13, wherein the gauge support includes a gauge support body defining a gauge cavity configured to receive a portion of the pin, wherein the gauge cavity defines a support interior surface defining a boundary of the gauge cavity, and wherein the support interior surface is configured to mechanically engage the pin when the gauge support mechanically engages the pin.

Example 15: The system of any of examples 12-14, wherein the pin includes a pin body defining a pin exterior surface, and wherein the support interior surface is configured to mechanically engage the pin exterior surface when the gauge support mechanically engages the pin.

Example 16: The system of any of examples 12-15, wherein the gauge support is configured to slidably translate when a force is exerted on the gauge support as the gauge support mechanically engages the pin.

Example 17: The system of any of examples 12-16, wherein the gauge support is configured to substantially surround a perimeter of the pin when the gauge support mechanically engages the pin.

Example 18: The system of any of examples 12-17, wherein the gauge support is configured to form a snap fit with at least a portion of the perimeter of the pin when the gauge support mechanically engages the pin.

Example 19: The system of any of examples 12-18, wherein the gauge support includes a gauge support body defining a pin access configured to allow the pin to pass therethrough when the gauge support mechanically engages the pin.

Example 20: The system of any of examples 12-19, further comprising a gauge base mechanically supported by the gauge support, and wherein the gauge base is configured to define the x displacement and the y-displacement when the gauge support mechanically engages the pin.

Example 21: The system of example 20, wherein: the gauge base is configured to define a center point when the gauge support mechanically engages the pin, the gauge base includes one or more visible indicia on the gauge base, and each visible indicia is configured to define at least one of: an x-distance from the center point to define the x displacement, wherein the x-distance is substantially parallel to the x axis, or a y-distance from the center point to define the y displacement, wherein the y-distance is substantially parallel to the y axis.

Example 22: The system of example 21, wherein the one or more visible indicia define one or more circles centered on the center point.

Example 23: The system of example 21, wherein the one or more visible indicia define a grid, wherein the grid defines one or more lines substantially parallel to the x axis intersecting one or more lines substantially parallel to the y axis.

Example 24: The system of any of examples 21-23, wherein the gauge support is configured to provide the output viewable by the practitioner using the x-distance and the y-distance defined by the one or more visible indicia when the pointer tip and the target point define the x displacement and the y displacement.

Example 25: The system of any of examples 12-24, further comprising a z-member attached to the gauge support, wherein the z-member is configured to define the z displacement when the gauge support mechanically engages the pin.

Example 26: The system of example 25, wherein: the gauge base is configured to define a center point when the gauge support mechanically engages the pin, the z-member includes one or more visible indicia on the gauge base, and each visible indicia is configured to define a z-distance from the center point to define the z displacement, wherein the z-distance is substantially parallel to the z axis.

Example 27: The system of example 26, wherein the one or more visible indicia define one or more lines substantially parallel to one of the x axis or the y axis.

Example 28: The system of example 26 or example 27, wherein the gauge support is configured to provide the output viewable by the practitioner using the z-distance defined by the one or more visible indicia when the pointer tip and the target point define the z displacement.

Example 29: The system of any of examples 12-28, wherein: the gauge support is configured to mechanically engage a pin body of the pin extending from a phantom support base of the phantom base to the target point, the gauge support body mechanically supports a z-member configured to define the z displacement, the gauge support is configured to define a z-altitude of the z-member when the gauge support body contacts the phantom support base, and the z-altitude is substantially parallel to the z axis.

Example 30: The system of any of examples 12-29, wherein: the gauge support defines a gauge axis passing through a center point defined by the gauge support, the gauge support is configured to define at least one of an x-distance from the center point to define the x displacement, a y-distance from the center point to define the y displacement, or a z-distance from the center point to define the z displacement, the gauge support is configured to mechanically engage a pin body of the pin extending from a phantom support base of the phantom base to the target point and defining a pin axis passing through the pin body from the phantom base to the target point, and the stereotactic accuracy gauge is configured to substantially align the pin axis with the gauge axis when the gauge support mechanically engages the pin body.

Example 31: The system of example 1, further comprising: one or more cameras, wherein the one or more cameras define a first field of view and define a second field of view; and processing circuitry configured to, receive a first image from the one or more cameras, wherein the first image defines a first target location and a first pointer location, wherein the first target location defines a first imaged location of the target point in the first field of view and the first pointer location defines a first imaged location of the pointer tip in the first field of view, receive a second image from the one or more cameras, wherein the second image defines second target location and a second pointer location, wherein the second target location defines a second imaged location of the target point in the second field of view and the second pointer location defines a second imaged location of the pointer tip in the second field of view, compare the first point location, the first pointer location, the second target location, and the second pointer location to determine one or more of the x displacement, the y displacement, or the z displacement, and provide the output to a display.

Example 32: The system of example 31, wherein: the one or more cameras are configured to define the first target location and define the first pointer location using a first image coordinate system defined in the first field of view by the one or more cameras, the one or more cameras are configured to define the second target location and define the second pointer location using a second image coordinate system defined in the second field of view by the one or more cameras, and the processing circuitry is configured to compare the first point location, the first pointer location, the second target location, and the second pointer location using the first image coordinate system and the second image coordinate system.

Example 33: The system of example 32, wherein the system is configured to define at least one of: an orientation of the first image coordinate system relative to the x-y-z coordinate system, or an orientation of the second image coordinate system relative to the x-y-z coordinate system.

Example 34: The system of example 33, wherein the processing circuitry is configured to compare the first point location, the first pointer location, the second target location, and the second pointer location using at least one: the defined orientation of the first image coordinate system, or the defined orientation of the second image coordinate system.

Example 35: The system of example 33 or 34, wherein the processing circuitry is configured map at least one of: the defined orientation of the first image coordinate system to the x-y-z coordinate system, or the defined orientation of the second image coordinate system to the x-y-z coordinate system.

Example 36: The system of any of examples 31-35, wherein the processing circuitry is configured to: recognize at least one of the first target location or the first pointer location in the first image using image recognition software;

recognize at least one of the second target location or the second pointer location in the second image using the image recognition software; and compare the first point location, the first pointer location, the second target location, and the second pointer location using at least one of the recognized first target location, the recognized first pointer location, the recognized second target location, or the recognized second pointer location.

Example 37: The system of any of examples 31-36, further comprising a gauge frame configured to mechanically engage the phantom base, wherein the gauge frame mechanically supports the one or more cameras.

Example 38: The system of example 37, wherein the x-y-z coordinate system is a primary coordinate system defined by the phantom base, wherein the gauge frame defines a secondary x-y-z coordinate system, and wherein the gauge support is configured to substantially align the secondary coordinate system with the primary coordinate system when the gauge frame mechanically engages the phantom base.

Example 39: The system of example 37 or example 38, wherein the gauge frame is configured to establish a position of the one or more cameras with respect to the target point when the gauge frame mechanically engages the phantom base and mechanically supports the one or more cameras.

Example 40: The system of any of examples 37-39, wherein the gauge frame mechanically supports a wall defining a backdrop surface, wherein the gauge frame is configured to position the backdrop surface in the first field of view when the gauge frame mechanically supports the one or more cameras.

Example 41: The system of example 40, wherein the gauge frame is configured to position the target point of the phantom base between the one or more cameras and the backdrop surface when the gauge frame mechanically engages the phantom base.

Example 42: The system of any of examples 37-41, wherein the gauge frame mechanically supports a wall defining a backdrop surface, wherein the gauge frame is configured to position the backdrop surface in the second field of view when the gauge frame mechanically supports the second camera.

Example 43: The system of any of examples 37-42, wherein the gauge frame is configured to maintain the first field of view substantially stationary with respect to the phantom base and maintain the second field of view substantially stationary with respect to the phantom base when the gauge frame mechanically engages the phantom base and mechanically supports the one or more cameras.

Example 44: The system of any of examples 37-43, wherein the gauge frame is configured to cause the first field of view defined by the one or more cameras to intersect the second field of view defined by the one or more cameras when the gauge frame mechanically supports the one or more cameras.

Example 45: The system of any of examples 37-43, wherein the one or more cameras include a first camera configured to translate in at least one of a direction parallel to the x axis, a direction parallel to the y axis, or a direction parallel to the z axis when the gauge frame mechanically supports the first camera.

Example: A method, comprising: defining, with a system, an x displacement from a target point of a phantom base mechanically engaging the a stereotactic frame to a pointer tip of the stereotactic frame when the pointer tip is placed at a pointer tip location in proximity to the target point, wherein the x displacement is a distance parallel to an x axis in an x-y-z coordinate system; defining, with the system, a y displacement from the target point to the pointer tip when the pointer tip is placed in the pointer tip location, wherein the y displacement is a distance parallel to a y axis in the x-y-z coordinate system; defining, with the system, a z displacement from the target point to the pointer tip when the pointer tip is placed in the pointer tip location, wherein the z displacement is a distance parallel to a z axis in the x-y-z coordinate system; and providing, with the system, an output viewable by a practitioner, wherein the output indicates one or more of the x displacement, the y displacement, or the z displacement.

Example 47: The method of example 46, further comprising maintaining a portion of the system substantially stationary relative to the target point of the phantom base.

Example 48: The method of example 46 or example 47, wherein the pointer the pointer tip location is a first pointer tip location, and further comprising: defining, using the system, a second x displacement when the pointer tip is placed in a second pointer tip location, a second y displacement when the pointer tip is placed in the second pointer tip location, and a second z displacement when the pointer tip is placed in the second pointer tip location; and providing, using the system, a second output viewable by a practitioner, wherein the second output indicates one or more of the second x displacement, the second y displacement, and the second z displacement.

Example 49: The method of any of examples 46-48, further comprising defining the x-y-z coordinate system using the system.

Example 50: The method of any of examples 46-49, further comprising mechanically engaging a gauge support of the system with a pin of the phantom base, wherein the pin defines the target point.

Example 51: The method of example 50, further comprising aligning a secondary coordinate system with the x-y-z coordinate system when the gauge support mechanically engages the pin, wherein the gauge support defines the secondary x-y-z coordinate system and the phantom base define the x-y-z coordinate system.

Example 52: The method of example 50 or example 51, further comprising mechanically engaging a support interior surface with the pin, wherein a gauge support body of the gauge support defines a gauge cavity configured to receive a portion of the pin and the gauge cavity defines the support interior surface defining a boundary of the gauge cavity.

Example 53: The method of any of examples 50-52, further comprising slidably translating the gauge support when the gauge support mechanically engages the pin.

Example 54: The method of any of examples 50-53, further comprising defining the x displacement and the y displacement using one or more visible indicia of a gauge base configured to define a center point when the gauge support mechanically engages the pin, wherein each visible indicia is configured to define at least one of an x-distance from the center point or a y-distance from the center point, wherein the x-distance is substantially parallel to the x axis and the y-distance is substantially parallel to the y axis, and wherein the gauge support mechanically supports the gauge base.

Example 55: The method of any of examples 50-54, further comprising: defining a center point using the gauge support when the gauge support mechanically engages the pin; and defining the z displacement using one or more visible indicia of a z-member secured to the gauge support, wherein each visible indicia is configured to define a z-distance from the center point.

Example 56: The method of any of examples 50-55 further comprising: defining a z-altitude of a z-member configured to define the z displacement when a gauge support body of the gauge supports contacts a phantom support base mechanically supporting a pin body of the pin extending from the phantom support base to the target point.

Example 57: The method of any of examples 50-56, further comprising aligning a gauge support axis passing through a center point defined by the gauge support with a pin axis passing through a pin body of the pin when the gauge support mechanically engages the pin body, wherein the pin extends from a phantom support base to the target point and defines the pin axis passing through the pin body from the phantom base to the target point.

Example 58: The method of any of examples 46-49, further comprising: defining a first field of view using one or more cameras of the system, defining a second field of view using the one or more cameras of the system, receiving, by processing circuitry, a first image from the one or more cameras, wherein the first image defines a first target location and a first pointer location, wherein the first target location defines a first imaged location of the target point in the first field of view and the first pointer location defines a first imaged location of the pointer tip in the first field of view, receiving, by the processing circuitry, a second image from the one or more cameras, wherein the second image defines second target location and a second pointer location, wherein the second target location defines a second imaged location of the target point in the second field of view and the second pointer location defines a second imaged location of the pointer tip in the second field of view, comparing, by the processing circuitry, the first point location, the first pointer location, the second target location, and the second pointer location to determine one or more of the x displacement, the y displacement, or the z displacement, and providing, by the processing circuitry, the output to a display.

Example 59: The method of example 58, further comprising: defining, by at least one of the processing circuitry or the first camera, the first target location and the first pointer location using a first image coordinate system defined by the one or more cameras, defining, by at least one of the processing circuitry or the second camera, the second target location and the second pointer location using a second image coordinate system defined by the one or more cameras, and comparing, using the processing circuitry, the first point location, the first pointer location, the second target location, and the second pointer location using the first image coordinate system and the second image coordinate system.

Example 60: The method of example 58 or 59, further comprising: defining, using the system, at least one of: an orientation of the first image coordinate system relative to the x-y-z coordinate system, or an orientation of the second image coordinate system relative to the x-y-z coordinate system; and mapping, using the processing circuitry, at least one of: the defined orientation of the first image coordinate system to the x-y-z coordinate system, or the defined orientation of the second image coordinate system to the x-y-z coordinate system.

Example 61: The method of any of examples 58-60, further comprising: recognizing, using image recognition software of the processing circuitry, at least one of the first target location or the first pointer location in the first image; recognizing, using the image recognition software of the processing circuitry, at least one of the second target location or the second pointer location in the second image; and comparing, using the processing circuitry, the first point location, the first pointer location, the second target location, and the second pointer location using at least one of the recognized first target location, the recognized first pointer location, the recognized second target location, or the recognized second pointer location.

Example 62: The method of any of examples 58-61, further comprising mechanically engaging a gauge frame and the phantom base, wherein the gauge frame mechanically supports the first camera and the second camera.

Example 63: The method of example 62, further comprising substantially aligning a primary coordinate system defined by the phantom base with a secondary coordinate system defined by the gauge frame when the gauge frame mechanically engages the phantom base.

Example 64: The method of example 62 or example 63, further comprising establishing a position of the first field of view with respect to the target point and establishing a position of the second field of view with respect to the target point when the gauge frame mechanically engages the phantom base.

Example 65: The method of any of examples 62-64, further comprising positioning a backdrop surface mechanically supported by the frame gauge within at least one of the first field of view or the second field of view when the gauge frame mechanically engages the phantom base.

Example 66: The method of any of examples 62-65, further comprising maintaining the first field of view substantially stationary with respect to the phantom base using the gauge frame and maintaining the second field of view substantially stationary with respect to the phantom base using the gauge frame when the gauge frame mechanically engages the phantom base.

Example 67: The method of any of examples 62-66, further comprising translating a first camera of the one or more cameras in at least one of a direction parallel to the x axis, a direction parallel to the y axis, or a direction parallel to the z axis when the gauge frame mechanically supports the first camera.

Example 68: A stereotactic accuracy gauge configured to define an x-y-z displacement from a pin tip of a phantom base configured to simulate an intercranial space, the stereotactic accuracy gauge comprising: a gauge base defining an x-y plane, wherein the gauge base defines a pin access opening and the pin access opening defines a center point; a z-member attached to the gauge base, wherein the z-member defines a z-direction substantially perpendicular to the x-y plane; and a gauge support mechanically supporting the gauge base, wherein the gauge support is configured to mechanically engage a pin defining the pin tip, wherein the pin access is configured to allow the pin to pass therethrough when the gauge support contacts the phantom base, and wherein the stereotactic accuracy gauge is configured to define a displacement in the x-y plane and a displacement in the z-direction between a point in the simulated intercranial space and the center point of the pin access opening.

Example 69: The stereotactic accuracy gauge of example 68, wherein the gauge support defines a fixed displacement from the gauge base, and wherein the gauge support is configured to contact the phantom base.

Example 70: The stereotactic accuracy gauge of example 68 or example 69, wherein: the gauge base includes one or more x-y visible indicia on the gauge base, wherein each x-y visible indicia indicates the displacement in the x-y plane between the each x-y visible indicia and the center point, and the z-member includes one or more z visible indicia on the z-member, wherein each z visible indicia indicates the displacement in the z-direction between the each z visible indicia and the center point.

Example 71: The stereotactic accuracy gauge of any of examples 68-70, wherein the stereotactic accuracy gauge is configured to allow a pin axis defined by the pin and passing through the pin tip to substantially intersect the center point of the pin access when the stereotactic accuracy gauge contacts the support base and the pin passes through the pin access.

Example 72: The stereotactic accuracy gauge of example 70 or example 71, wherein the x-y visible indicia define a plurality of concentric circles surrounding the pin access opening, wherein the plurality of concentric circles are centered on the center point of the pin access opening.

Example 73: The stereotactic accuracy gauge of any of examples 68-72, wherein the x-y visible indicia define a plurality of cartesian coordinates, wherein each cartesian coordinate defines an x-coordinate and a y-coordinate in the x-y plane.

Example 74: The stereotactic accuracy gauge of any of examples 68-73, wherein the gauge support includes a gripping element configured to frictionally engage the pin when the gauge support mechanically engages the pin.

Example 75: The stereotactic accuracy gauge of example 74, wherein the gauge support is configured to slidably translate on the pin when the gripping element frictionally engages the pin.

Example 76: The system of any of examples 68-75, wherein the gauge support includes a gauge support body defining a gauge cavity configured to receive a portion of the pin, wherein the gauge cavity defines a support interior surface defining a boundary of the gauge cavity, and wherein the support interior surface is configured to mechanically engage the pin when the gauge support mechanically engages the pin.

Example 77: The system of any of examples 68-76, wherein the gauge support is configured to substantially surround a circumference of the pin when the gauge support mechanically engages the pin.

Example 78: The system of any of examples 68-77, wherein the stereotactic accuracy system defines one or more x-y visible indicia configured to define the displacement in the x-y plane, wherein the x-y visible indicia define one or more circles centered on the center point.

Example 79: The system of any of example 68-77, wherein the stereotactic accuracy system defines one or more x-y visible indicia configured to define the displacement in the x-y plane, wherein the one or more visible indicia define a grid, wherein the grid defines one or more lines substantially parallel to an x-axis defining the x-y plane and one or more lines substantially parallel to a y-axis defining the x-y plane.

Example 80: A system configured to configured to define an x-displacement, a y-displacement, and a z-displacement from a target point defined by a phantom base to a pointer tip of a pointer of a stereotactic system, the accuracy system comprising: one or more cameras, wherein the one or more cameras define a first field of view and define a second field of view; and processing circuitry configured to, receive a first image from the one or more cameras, wherein the first image defines a first target location and a first pointer location, wherein the first target location defines a first imaged location of the target point in the first field of view and the first pointer location defines a first imaged location of the pointer tip in the first field of view, receive a second image from the one or more cameras, wherein the second image defines second target location and a second pointer location, wherein the second target location defines a second imaged location of the target point in the second field of view and the second pointer location defines a second imaged location of the pointer tip in the second field of view, compare the first point location, the first pointer location, the second target location, and the second pointer location to determine one or more of the x displacement, the y displacement, or the z displacement, and provide the output to a display.

Example 81: The system of example 80, wherein: the one or more cameras are configured to define the first target location and define the first pointer location using a first image coordinate system defined in the first field of view by the one or more cameras, the one or more cameras are configured to define the second target location and define the second pointer location using a second image coordinate system defined in the second field of view by the one or more cameras, and the processing circuitry is configured to compare the first point location, the first pointer location, the second target location, and the second pointer location using the first image coordinate system and the second image coordinate system.

Example 82: The system of example 81, wherein the system is configured to define at least one of: an orientation of the first image coordinate system relative to the x-y-z coordinate system, or an orientation of the second image coordinate system relative to the x-y-z coordinate system.

Example 83: The system of example 82, wherein the processing circuitry is configured to compare the first point location, the first pointer location, the second target location, and the second pointer location using at least one: the defined orientation of the first image coordinate system, or the defined orientation of the second image coordinate system.

Example 84: The system of example 82 or 83, wherein the processing circuitry is configured map at least one of: the defined orientation of the first image coordinate system to the x-y-z coordinate system, or the defined orientation of the second image coordinate system to the x-y-z coordinate system.

Example 85: The system of any of examples 80-84, wherein the processing circuitry is configured to: recognize at least one of the first target location or the first pointer location in the first image using image recognition software; recognize at least one of the second target location or the second pointer location in the second image using the image recognition software; and compare the first point location, the first pointer location, the second target location, and the second pointer location using at least one of the recognized first target location, the recognized first pointer location, the recognized second target location, or the recognized second pointer location.

Example 86: The system of any of examples 80-85, further comprising a gauge frame configured to mechanically engage the phantom base, wherein the gauge frame mechanically supports the one or more cameras.

Example 87: The system of example 86, wherein the x-y-z coordinate system is a primary coordinate system defined by the phantom base, wherein the gauge frame defines a secondary x-y-z coordinate system, and wherein the gauge support is configured to substantially align the secondary coordinate system with the primary coordinate system when the gauge frame mechanically engages the phantom base.

Example 88: The system of example 86 or example 87, wherein the gauge frame is configured to establish a position of the one or more cameras with respect to the target point when the gauge frame mechanically engages the phantom base and mechanically supports the one or more cameras.

Example 89: The system of any of examples 86-88, wherein the gauge frame is configured to maintain the first field of view substantially stationary with respect to the phantom base and maintain the second field of view substantially stationary with respect to the phantom base when the gauge frame mechanically engages the phantom base and mechanically supports the one or more cameras.

Example 90: The system of any of examples 86-89, wherein the gauge frame is configured to cause the first field of view defined by the one or more cameras to intersect the second field of view defined by the one or more cameras when the gauge frame mechanically supports the one or more cameras.

Example 91: The system of any of examples 86-90, wherein the one or more cameras include a first camera configured to translate in at least one of a direction parallel to the x axis, a direction parallel to the y axis, or a direction parallel to the z axis when the gauge frame mechanically supports the first camera.

Example 92: The system of any of examples 80-91, further comprising a probe tip configured to mechanically engage the pointer of the stereotactic system, wherein the probe tip is configured to remain substantially stationary with respect to the pointer tip when the probe tip mechanically engages the pointer.

Example 93: The system of any of examples 80-92, further comprising a reflective paint configured to be applied to at least one of the pointer tip of the stereotactic system or the target point defined by the phantom base.

Various examples of the disclosure have been described. Any combination of the described accuracy systems, operations, or functions is contemplated. These and other examples are within the scope of the following claims.

What is claimed is:

1. A system configured to determine an accuracy of a stereotactic frame comprising translatable components configured to position a pointer tip at a real-space target in an x-y-z coordinate system, wherein the system is configured to:

define an x displacement from a target point of a phantom base mechanically engaging the stereotactic frame to the pointer tip of the stereotactic frame when the pointer tip is placed at a pointer tip location, wherein the x displacement is a distance parallel to an x axis in the x-y-z coordinate system, and wherein the target point defines the real-space target;

define a y displacement from the target point to the pointer tip when the pointer tip is placed in the pointer tip location, wherein the y displacement is a distance parallel to a y axis in the x-y-z coordinate system;

define a z displacement from the target point to the pointer tip when the pointer tip is placed in the pointer tip location, wherein the z displacement is a distance parallel to a z axis in the x-y-z coordinate system, wherein the x displacement, the y displacement, and the z displacement defines the accuracy of the positioning of the pointer tip at the real-space target by the stereotactic frame; and provide an output viewable by a practitioner, wherein the output indicates one or more of the x displacement, the y displacement, or the z displacement.

2. The system of claim 1, wherein the system defines the x-y-z coordinate system, wherein a portion of the system is configured to remain substantially stationary relative to a point in the x-y-z coordinate system, wherein the system is configured to map the x-y-z coordinate system to a coordinate system defined by the phantom base.

3. The system of claim 1, wherein the x-y-z coordinate system defines one or more locations in an intercranial space of a patient, and wherein the system is configured to at least one of:

define at least one of the x displacement or the y displacement on a horizontal anatomical plane defined by the intercranial space, and define the z displacement on at least one of a medial anatomical plane defined by the intercranial space or a coronal anatomical plane defined by the intercranial space of the patient; or define one of the x displacement or the y displacement substantially parallel to an anterior or posterior direction of the patient and define the other of the x displacement or the y displacement substantially parallel to a left lateral or a right lateral direction of the patient and define the z displacement substantially parallel to a superior or inferior direction of the patient.

4. The system of claim 1, further comprising a gauge support configured to mechanically engage a pin of the phantom base, wherein the pin defines the target point.

5. The system of claim 4, wherein the x-y-z coordinate system is a primary coordinate system defined by the phantom base, wherein the gauge support defines a secondary x-y-z coordinate system, and wherein the gauge support is configured to substantially align the secondary coordinate system with the primary coordinate system when the gauge support mechanically engages the pin.

6. The system of claim 4, wherein the gauge support includes a gauge support body defining a gauge cavity configured to receive a portion of the pin, wherein the gauge cavity defines a support interior surface defining a boundary of the gauge cavity, and wherein the support interior surface is configured to mechanically engage the pin when the gauge support mechanically engages the pin.

7. The system of claim 4, wherein the gauge support is configured to substantially surround a perimeter of the pin when the gauge support mechanically engages the pin.

8. The system of claim 4, further comprising a gauge base mechanically supported by the gauge support, wherein the gauge base includes:

one or more visible indicia on the gauge base, and wherein each visible indicia is configured to define at least one of:

an x-distance from the center point to define the x displacement, wherein the x-distance is substantially parallel to the x axis, or a y-distance from the center point to define the y displacement, wherein the y-distance is substantially parallel to the y axis; and a z-member attached to the gauge support, wherein the z-member is configured to define the z displacement when the gauge support mechanically engages the pin.

9. The system of claim 1, further comprising:

one or more cameras, wherein the one or more cameras define a first field of view and define a second field of view; and processing circuitry configured to, receive a first image from the one or more cameras, wherein the first image defines a first target location and a first pointer location, wherein the first target location defines a first imaged location of the target point in the first field of view and the first pointer location defines a first imaged location of the pointer tip in the first field of view, receive a second image from the one or more cameras, wherein the second image defines second target location and a second pointer location, wherein the second target location defines a second imaged location of the target point in the second field of view and the second pointer location defines a second imaged location of the pointer tip in the second field of view, compare the first point location, the first pointer location, the second target location, and the second pointer location to determine one or more of the x displacement, the y displacement, or the z displacement, and provide the output to a display.

10. The system of claim 9, wherein:

the one or more cameras are configured to define the first target location and define the first pointer location using a first image coordinate system defined in the first field of view by the one or more cameras, the one or more cameras are configured to define the second target location and define the second pointer location using a second image coordinate system defined in the second field of view by the one or more cameras, and the processing circuitry is configured to compare the first point location, the first pointer location, the second target location, and the second pointer location using the first image coordinate system and the second image coordinate system.

11. The system of claim 10, wherein the system is configured to define at least one of:

an orientation of the first image coordinate system relative to the x-y-z coordinate system, or an orientation of the second image coordinate system relative to the x-y-z coordinate system.

12. The system of claim 11, wherein the processing circuitry is configured map at least one of:

the defined orientation of the first image coordinate system to the x-y-z coordinate system, or the defined orientation of the second image coordinate system to the x-y-z coordinate system.

13. The system of claim 9, wherein the processing circuitry is configured to:

recognize at least one of the first target location or the first pointer location in the first image using image recognition software;

recognize at least one of the second target location or the second pointer location in the second image using the image recognition software; and compare the first point location, the first pointer location, the second target location, and the second pointer location using at least one of the recognized first target location, the recognized first pointer location, the recognized second target location, or the recognized second pointer location.

14. The system of claim 9, further comprising a gauge frame configured to mechanically engage the phantom base, wherein the gauge frame mechanically supports the one or more cameras.

15. The system of claim 14, wherein the x-y-z coordinate system is a primary coordinate system defined by the phantom base, wherein the gauge frame defines a secondary x-y-z coordinate system, and wherein the gauge frame is configured to substantially align the secondary coordinate system with the primary coordinate system when the gauge frame mechanically engages the phantom base.

16. The system of claim 14, wherein the gauge frame is configured to establish a position of the one or more cameras with respect to the target point when the gauge frame mechanically engages the phantom base and mechanically supports the one or more cameras, and wherein the gauge frame is configured to cause the first field of view defined by the one or more cameras to intersect the second field of view defined by the one or more cameras when the gauge frame mechanically supports the one or more cameras.

17. The system of claim 1, further comprising an accuracy finder configured to engage the stereotactic frame, wherein the accuracy finder comprises:

a range finder configured to determine a range to the pointer tip; and processing circuitry configured to:

determine a separation of the pointer tip from the target point, wherein the separation is indicative of a number of degrees by separating the pointer tip from the target point; and determine the x displacement, the y displacement, and the z displacement using the separation and the range.

18. A system configured to determine an accuracy of a stereotactic frame comprising translatable components configured to position a pointer tip at a real-space target in an x-y-z coordinate system, wherein the system is configured to:

define the x-y-z coordinate system;

define an x displacement from a target point of a phantom base mechanically engaging the stereotactic frame to the pointer tip of the stereotactic frame when the pointer tip is placed at a pointer tip location, wherein the x displacement is a distance parallel to an x axis in the x-y-z coordinate system, and wherein the target point defines the real-space target;

define a y displacement from the target point to the pointer tip when the pointer tip is placed in the pointer tip location, wherein the y displacement is a distance parallel to a y axis in the x-y-z coordinate system;

define a z displacement from the target point to the pointer tip when the pointer tip is placed in the pointer tip location, wherein the z displacement is a distance parallel to a z axis in the x-y-z coordinate system, wherein the system is configured to at least one:

define at least one of the x displacement or the y displacement on a horizontal anatomical plane defined by an intercranial space of a patient, and define the z displacement on at least one of a medial anatomical plane defined by the intercranial space or a coronal anatomical plane defined by the intercranial space of the patient; or define one of the x displacement or the y displacement substantially parallel to an anterior or posterior direction of the patient and define the other of the x displacement or the y displacement substantially parallel to a left lateral or a right lateral direction of the patient and define the z displacement substantially parallel to a superior or inferior direction of the patient, wherein the x displacement, the y displacement, and the z displacement defines the accuracy of the positioning of the pointer tip at the real-space target by the stereotactic frame; and map the x-y-z coordinate system to a coordinate system defined by the phantom base; and provide an output viewable by a practitioner, wherein the output indicates one or more of the x displacement, the y displacement, or the z displacement mapped to the coordinate system defined by the phantom base.

19. A method, comprising:

defining, with a system, an x displacement from a target point of a phantom base mechanically engaging a stereotactic frame to a pointer tip of the stereotactic frame when the pointer tip is placed at a pointer tip location in proximity to the target point, wherein the x displacement is a distance parallel to an x axis in an x-y-z coordinate system, the stereotactic frame comprising translatable components configured to position the pointer tip at a real-space target in the x-y-z coordinate system, wherein the target point defines the real-space target;

defining, with the system, a y displacement from the target point to the pointer tip when the pointer tip is placed in the pointer tip location, wherein the y displacement is a distance parallel to a y axis in the x-y-z coordinate system;

defining, with the system, a z displacement from the target point to the pointer tip when the pointer tip is placed in the pointer tip location, wherein the z displacement is a distance parallel to a z axis in the x-y-z coordinate system; and providing, with the system, an output viewable by a practitioner, wherein the output indicates one or more of the x displacement, the y displacement, or the z displacement to determine the accuracy of the positioning of the pointer tip at the real-space target by the stereotactic frame.

20. The method of claim 19, further comprising:

defining, using the system, the x-y-z coordinate system, wherein a portion of the system is configured to remain substantially stationary relative to a point in the x-y-z coordinate system; and mapping, using the system, the x-y-z coordinate system to a coordinate system defined by the phantom base.

* * * * *